(12) United States Patent
Taniguchi et al.

(10) Patent No.: US 6,238,535 B1
(45) Date of Patent: May 29, 2001

(54) HYDROCARBON SENSOR

(75) Inventors: Noboru Taniguchi, Osaka; Masuo Takigawa, Nara, both of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/280,522

(22) Filed: Apr. 5, 1999

(30) Foreign Application Priority Data

| Apr. 6, 1998 | (JP) | 10-093340 |
| May 25, 1998 | (JP) | 10-142710 |

(51) Int. Cl.$^7$ ................................ G01N 27/407
(52) U.S. Cl. ............... 204/424; 204/425; 204/426; 204/292; 204/293; 205/784.5; 205/787
(58) Field of Search ............ 204/421–429, 204/292, 293

(56) References Cited

U.S. PATENT DOCUMENTS

| 4,785,658 | 11/1988 | Jackson | 73/23 |
| 5,451,310 | * 9/1995 | Behl et al. | 204/426 |
| 5,510,013 | * 4/1996 | Hippe et al. | 204/426 |
| 5,798,270 | 8/1998 | Adamczyk, Jr. et al. | 436/143 |
| 5,935,398 | * 8/1999 | Taniguichi et al. | 204/426 |

FOREIGN PATENT DOCUMENTS

| 9-127055 | 5/1997 | (JP) . |
| 10-300718 | 11/1998 | (JP) . |

OTHER PUBLICATIONS

Inaba et al., "Limiting Current Sensor Using Proton Conduction Thin–Film", Chemical Sensor, 1995, Month Unavailable vol. 11, Supplement B, pp. 145–148.

* cited by examiner

Primary Examiner—T. Tung
(74) Attorney, Agent, or Firm—Wenderoth, Lind & Ponack, L.L.P.

(57) ABSTRACT

The present invention relates to a limiting-current type hydrocarbon sensor comprising a solid-electrolytic layer made of a Ba—Ce-based oxide, and provides a sensor capable of stably detecting hydrocarbon at high sensitivity, regardless of the concentration of oxygen in an atmosphere. A material mainly containing Al is used for at least one of two electrodes on the solid-electrolytic layer made of a Ba—Ce-based oxide to block oxygen at the electrode, i.e. cathode, whereby a hydrocarbon sensor being stable, high in sensitivity, compact, easy to use and low in cost can be provided. Furthermore, the other electrode, anode, of the limiting-current type hydrocarbon sensor is made of a material mainly containing Ag. The limiting-current type hydrocarbon sensor comprises a thin sensor-use solid-electrolytic layer capable of conducting protons and oxide ions, a pair of sensor-use electrodes formed on both sides of the solid-electrolytic layer, one electrode on each side, and a gas diffusion rate determining layer formed on the side of the cathode, one of the pair of electrodes. On the sensor-use solid-electrolytic layer on the side of the anode, a solid ion pump for transferring oxygen, hydrogen or water vapor is provided between the anode and the atmosphere under measurement.

26 Claims, 16 Drawing Sheets

HYDROCARBON SENSOR

FIELD OF THE INVENTION

The present invention relates to a hydrocarbon sensor formed of a solid electrolyte for detecting hydrocarbon and for measuring the concentration thereof in an atmosphere in the temperature range of about 300° C. to 800° C.

PRIOR ART

Hydrocarbon sensors can be used to detect hydrocarbons in living environments and hydrocarbons included in exhaust discharged from vehicle engines, combustion heaters and catalytic converters, and to measure the concentration thereof. In particular, hydrocarbon sensors are used as lean-burn controlling sensors for vehicle engines and combustion apparatuses. As a conventional device for measuring or detecting hydrocarbons, a solid-electrolytic type sensor is known.

Since the solid-electrolytic hydrocarbon sensor is used in a high-temperature atmosphere, for example, in exhaust gas from combustion engines and the like, a proton based on an oxide capable of functioning at room temperature or more is used for the sensor. As the solid-electrolytic sensor, an electromotive-force type sensor and a limiting-current type sensor are known. For these sensors, a Ca—Zr-based oxide having a composition of $CaZr_{0.9}In_{0.1}O_{3-\alpha}$ has been developed as an oxide-based proton conductor, and an attempt is made to apply the oxide to hydrocarbon sensors.

For example, Proceedings of the 61st Conference (1994) pp99 of Electrochemical Society of Japan by Hibino, Tanaki and Iwahara have disclosed an electromotive-force type hydration sensor comprising Pd—Au alloyed electrodes as a hydrocarbon sensor formed of a Ca—Zr-based oxide electrolyte.

Furthermore, Inaba, Takahashi, Saji, Shiooka; Proceedings of the 21st Conference in 1995 Japan Association of Chemical Sensors pp145 have disclosed a limiting-current type hydrocarbon sensor having porous alumina as a diffusion rate determining layer.

However, the Ca—Zr-based oxide used as a solid electrolyte has a low proton conductivity of about $5 \times 10^{-4}$ S/cm at 600° C. In order to raise the sensitivity of the sensor, the operation temperature must be set at a high temperature of 700° C. or more in the case of the EMF type, or the electrolyte must be lowered in thickness to a thin layer in the case of the limiting-current type. Otherwise, it is difficult to use the sensor. For these reasons, solid-electrolytic materials having higher proton conductivity have been demanded.

Problems are also caused with respect to the detection mechanism and structure of the sensor formed of the Ca—Zr-based oxide. The EMF-type sensor cannot accurately detect hydrocarbons in an atmosphere where no oxygen is present or the concentration of oxygen changes significantly, since the sensor uses the catalytic function of electrodes. The limiting-current type sensor has difficulty in setting the electrolytic voltage of hydrocarbon, although the sensor uses porous alumina for its diffusion rate determining layer.

Accordingly, the inventors of the present invention have proposed a limiting-current type (or constant potential electrolytic type) hydrocarbon sensor formed of a Ba—Ce-based oxide having high proton conductivity (Japanese Laid-open Patent Publication No. 10-300718.

FIG. 19 shows a conventionally typical hydrocarbon sensor of limiting current type, which comprises a thin solid electrolyte layer 3 having high proton conductivity, two electrodes, anode 2 and cathode 4, attached on the both main surfaces of the solid electrolyte layer 3 and a diffusion rate determining layer formed on the side of the anode on the solid electrolytic layer. In this case, the diffusion rate determining layer has a substrate 1 formed a space (i.e., anode chamber 20) over the anode 2 and a through hole 61 between the substrate 1 and the electrolyte layer 3. The through hole 61 transfers gas components containing hydrocarbon from a atmosphere to be measured to the anode chamber 20 by diffusion when the sensor is disposed in a atmosphere to be measured to determine the hydrocarbon therein. In use of such a sensor, current between the electrodes, under application of a constant voltage, is measured in a process of transferring protons, which are dissociated catalytically on the anode from hydrocarbon, through the solid electrolyte layer to the cathode, then obtaining concentration of hydrocarbon in the atmosphere.

This sensor using Ba—Ce-based oxide layer as a solid electrolyte layer 3 satisfactorily responds to hydrocarbon and in the absence of oxygen in the atmosphere to be measured, can linearly detect hydrocarbon in a wide range of the order of several ppm to the order of several percents.

However, in the case where the concentration of hydrocarbon is very low (10 ppm or less) and an oxygen-free condition is changed to an oxygen-mixed condition, the sensor causes a phenomenon in which its output current between its electrodes through the electrolyte increases. This is because the Ba—Ce-based oxide used as an electrolyte has a characteristic of conducting oxide ions, whereby oxygen in an atmosphere can dissociate and transfer the electrolyte to the anode.

In order that hydrocarbon sensors are used to detect hydrocarbon in living environments and to measure the concentration of hydrocarbon in combustion exhaust discharged from vehicle engines and combustion apparatuses, such as heaters and the like, the hydrocarbon sensors requires high selectivity for hydrocarbon without being affected by the concentration of oxygen, even in such atmospheres including oxygen, and also requires high sensitivity and reliability by virtue of the high selectivity. Furthermore, hydrocarbon sensors must be directly disposed in atmospheres to be measured in many cases. Therefore, hydrocarbon sensors are desired to be compact, easy to use and low in production cost.

In a conventional limiting-current type hydrocarbon sensor, a Ba—Ce-based oxide having high proton conductivity is used for a thin electrolytic layer, a pair of electrodes is formed on both sides of the electrolyte, one electrode on each side, so as to be opposite to each other. The pair of electrodes is usually made of platinum.

In the case where this type of hydrocarbon sensor is used in such an environment including oxygen as described above, the sensor satisfactorily responds to hydrocarbon in the atmosphere. However, at the same time, its output changes owing to the existence of oxygen in the atmosphere, in particular, owing to the concentration of the oxygen, thereby causing large errors in the actually measured values. This phenomenon occurs as described below. Oxygen is taken in from the atmosphere on the cathode side, and ionized by the cathode made of platinum. Oxide ions thus generated at the cathode may pass through such a thin electrolytic layer, thereby causing current to flow across the two electrodes.

SUMMARY OF THE INVENTION

An object of the present invention is to provide a hydrocarbon sensor, formed of a solid electrolyte having high proton conductivity and also exhibiting conductivity of oxide ions, which is capable of highly accurately detecting only hydrocarbon included in an atmosphere to be measured without being affected by the existence of oxygen in the atmosphere.

Another object of the present invention is to provide a hydrocarbon sensor having high sensitivity, more particularly, a hydrocarbon sensor being insensitive to oxygen at the cathode on the solid electrolyte thereof and highly sensitive to only hydrocarbon at the anode.

First, generally speaking, the present invention provides a hydrocarbon sensor being insensitive to the concentration of oxygen in an atmosphere by using its cathode made of an electrode material being inactive with the oxygen in the atmosphere, instead of a conventional electrode made of platinum. The electrode material is selected to prevent the generation of oxygen ions on the surface of the electrode, thereby to prevent the entry of oxygen into the solid electrolyte.

The present invention thus provides a hydrocarbon sensor being insensitive to the concentration of oxygen in an atmosphere by providing a structure wherein the cathode is not exposed to the oxygen in the atmosphere to prevent oxygen from reaching the surface of the cathode, thereby to prevent oxygen from entering the solid electrolyte.

More specifically, the cathode of this sensor is made of Al or a material mainly containing Al. The present invention uses the fact that the surface of metal aluminum is inactivated catalytically with oxygen molecules, to prevent oxygen molecules from dissociating on the cathode and from transfer as partly dissociated ions to the electrolytic layer.

In particular, in the present invention, an aluminum oxide film may be coated on the Al-containing metal layer to form the cathode.

The solid electrolyte of the present invention is formed of a proton-oxide-ion mixing conductor and the cathode is made of Al coated with an aluminum oxide film to make the conductivity to oxide ions ineffective. This makes it possible to achieve a hydrocarbon sensor being insensitive to oxygen and highly sensitive to hydrocarbon.

Furthermore, in order to obtain an excellent sensing characteristic, an anode of the hydrocarbon sensor of the present invention is made of a material different from platinum which has been used conventionally. The anode in the present invention may preferably be made of a material mainly containing Ag to raise the sensitivity for detecting hydrocarbon, whereby the sensor can detect hydrocarbon at high accuracy.

Second, the present invention provides a limiting-current type hydrocarbon sensor, without detecting oxygen in the measured atmosphere, although sensor comprises a solid-electrolytic layer capable of highly conducting both protons and oxide ions. Such a hydrocarbon sensor further comprises a solid ion pump which supplies oxygen, hydrogen or water vapor to a cathode which is one of the pair of electrodes disposed on both sides of the sensor-use solid-electrolytic layer. The ion pump may substantially keep the transferring amount of oxygen from an atmosphere to the cathode constant.

With this configuration, the entry of oxygen into the cathode of the sensor from the atmosphere outside the sensor is controlled. As a result, the sensor can stably measure hydrocarbon in the atmosphere regardless of the concentration of oxygen in the atmosphere under measurement, and can obtain high measurement accuracy.

The solid ion pump formed in the sensor of the present invention comprises a pump-use solid-electrolytic layer capable of conducting oxide ions or protons, and a pair of pump-use electrodes disposed on both sides of the solid-electrolytic layer, one electrode on each side. The pump-use solid-electrolytic layer is disposed on the above-mentioned sensor-use solid-electrolytic layer on the cathode side with a space hermetically provided therebetween to form a hermetically sealed cathode chamber.

By driving such a solid ion pump by applying a constant voltage or current across the pump-use electrodes, oxygen, hydrogen or water vapor is supplied to or discharged from the hermetically sealed cathode chamber through the solid-electrolytic layer to control the concentration of oxygen in the cathode chamber to keep it substantially constant.

Furthermore, the solid-electrolytic layer used for the solid ion pump may easily be formed of an oxide ion conductor, a proton conductor, or a mixing ion conductor for the two kinds of ions. Oxygen, hydrogen or water vapor, or two kinds of them are transferred simultaneously to the cathode chamber in consideration of the polarities of the electrodes for the pump.

Additionally, the present invention provides an EMF-type sensor characterized in that a solid ion pump for supplying oxygen is mounted on the side of an inactive electrode, one of the pair of electrodes disposed on both sides of a sensor-use solid-electrolytic layer, one electrode on each side.

The solid ion pump comprises a pump-use solid-electrolytic layer capable of conducting oxide ions or protons, and a pair of pump-use electrodes disposed on both sides of the solid-electrolytic layer, one electrode on each side. The pump-use solid-electrolytic layer hermetically seals the upper surface of the above-mentioned sensor-use solid-electrolytic layer on the side of the inactive electrode thereof to form an inactive electrode chamber.

With this EMF-type sensor, the solid ion pump is driven by the application of a constant voltage or current, and oxygen is supplied to or discharged from the hermetically sealed inactive electrode chamber through the solid-electrolytic layer to control the concentration of oxygen in the inactive electrode chamber. Therefore, the inactive electrode chamber also functions as the standard electrode of the sensor, and an oxygen-hydrogen cell is formed across the chamber and the hydrocarbon active electrode, thereby making it possible to measure the concentration of hydrocarbon. Consequently, the sensor does not require any external standard electrode, and can accurately measure the concentration of hydrocarbon even in an atmosphere not including oxygen.

The hydrocarbon sensor of the present invention can operate in the temperature range from room temperature to high temperature (about 800° C.). The hydrocarbon sensor is thus advantageous in that it can be used widely as a sensor for detecting hydrocarbon leaking in living environments, and a sensor for measuring the concentration of hydrocarbon included in exhaust discharged from combustion engines, such as vehicle engines, and combustion apparatuses, such as heaters. In particular, the hydrocarbon sensor is suited for lean-burn control of combustion engines and apparatuses.

DETAILED DESCRIPTION OF THE INVENTION

Figure 1:
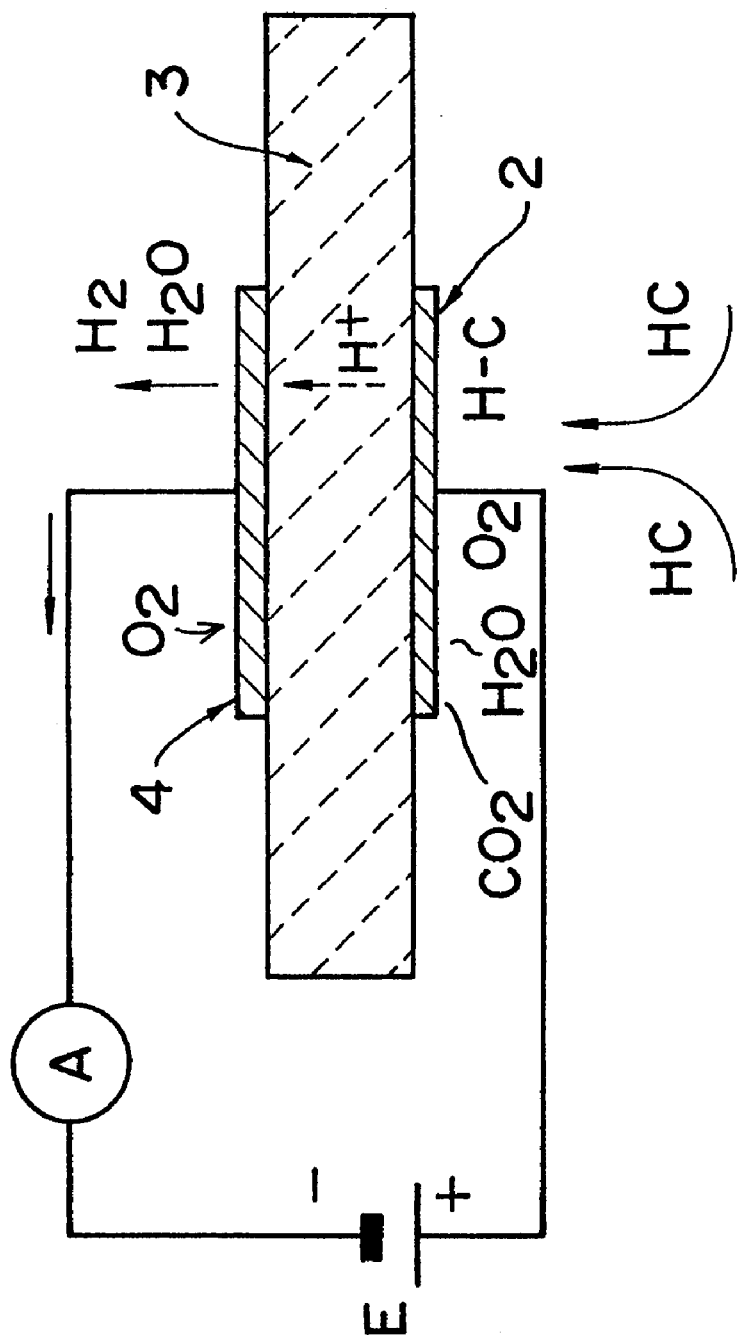
FIG. 1 is a schematic sectional view showing a hydrocarbon sensor in accordance with an example of the present invention.

First, a hydrocarbon sensor having a cathode formed of an aluminum-containing metal layer will be described below.

A hydrocarbon sensor in accordance with the present invention basically comprises a solid-electrolytic layer and a pair of electrodes mounted on both sides of the solid-electrolytic layer, one electrode on each side, so as to be opposite to each other. A cathode, any one of the pair of electrodes mounted on both sides of the solid-electrolytic layer is formed of an aluminum-containing metal layer.

The solid-electrolytic layer can be preferably formed of a thin ceramic layer made of a Ba—Ce-based oxide. Metal electrodes are formed on both sides of the layer, one electrode on each side, so as to be opposite to each other in the thickness direction. The solid-electrolytic layer is made of a barium-cerium-based oxide represented by a general formula of $BaCeO_{3-\alpha}$. The Ba—Ce-based oxide, in which part of cerium is substituted by another rare earth element, is used. For example, Y, Gd, Dy or the like is used as a substituent element. The other electrode, anode, can be made of Pt or another electrode material.

The cathode, one of the pair of electrodes of the sensor, is formed of a thin film mainly containing Al, on the surface of the ceramic layer. The Al-containing metal layer may be an aluminum layer directly formed of only aluminum or a layer made of an alloy material mainly containing Al.

Particularly, the cathode formed of the Al layer, an Al electrode for example, may be formed of a porous film including Al. The porous film of the electrode should preferably have such minute pores as to allow gas to pass through. Since the surface of the aluminum layer of the cathode is coated with a very thin oxide film, the aluminum by itself can prevent the dissociation of oxygen and can block the entry of oxygen into the electrolytic layer.

The Al-containing metal layer may contain Al as a base metal, and at least another element selected from among Si, Sn, Zn, Ga, In, Cd, Cu, Ag, Ni, Co, Fe, Mn and Cr and oxides of these.

By baking this mixture, the Al-containing metal layer can be formed by sintering as a porous film on the solid electrolyte.

In the sintered electrode formed of the Al-containing metal layer, the particles of the above-mentioned metals, such as Si, Sn or Zn, or oxides thereof hold Al particles to form a stable porous body. Part of the metal particles is alloyed with the Al particles, and forms a body sintered with the oxides. The other part of the metal particles prevents the drop of the Al particles and the collapse of the Al-containing metal layer, thereby stabilizing the cathode, even at the operation temperature of the sensor, not less than the melting point of Al, in particular.

In the Al-containing metal layer, the Al particles are connected to one another and brought into electrical conduction, thereby forming an electrode. The pores in the porous body are used as passages for hydrogen gas generated by the charges of protons having transferred through the solid-electrolytic layer from the anode, thereby dissipating the hydrogen gas to an atmosphere.

The sintered electrode formed of the Al-containing metal layer is made as described below. Aluminum and the other metals mentioned above are formed into powder and prepared in a paste form with a binder and a liquid such as water. The paste is applied into a layer on the surface of the solid-electrolytic layer, and then the solid-electrolytic layer is heated, the applied film being baked so as to be formed into the sintered electrode.

The cathode formed of the above-mentioned Al-containing metal layer is also applicable to a limiting-current type hydrocarbon sensor that uses a solid ion pump formed on the cathode side, as will be described later. By combination of the solid ion pump on the cathode side with the cathode formed of the Al-containing metal layer, the insensitivity of the sensor with respect to oxygen becomes far more significant, whereby it is possible to eliminate hydrocarbon measurement errors due to an amount of oxygen present in an atmosphere.

The other electrode, anode, may preferably be made of Ag, in particular. By using the anode made of Ag as the other electrode disposed opposite to the cathode formed of the above-mentioned Al-containing metal layer, it is possible to raise the sensitivity of detecting the concentration of hydrocarbon.

A content of Ag in the anode material mainly may be 50% or more, and the material may be mixed with about 10% of Pt. Furthermore, $SiO_2$ and the like may be mixed with Ag. The anode can be formed by screen printing and baking, sputtering, plating or the like.

Like the cathode, the anode can be made of Al. By using the electrodes both formed of the above Al-containing metal layer, the effect of blocking oxygen is recognized, and hydrocarbon can be detected. In this case, however, the sensitivity to hydrocarbon is lowered slightly.

In order to use the solid electrolytic layer as a limiting-current type hydrocarbon sensor, on which the cathode and the anode are formed, it requires that a diffusion rate determining layer be formed on the anode side of the solid electrolytic layer.

As an example of the diffusion rate determining layer, an anode chamber covered with a ceramic plate or substrate is formed on the surface of the solid electrolytic layer on the anode side, and a diffusion rate determining hole for communicating the anode chamber to an external atmosphere is formed between the ceramic plate and the solid electrolytic layer.

The diffusion rate determining hole is used to determine the diffusion amount of hydrocarbon through the through hole in proportion to the difference between the partial pressure of hydrocarbon in the anode chamber and that in the atmosphere outside the anode chamber. The diffusion rate determining hole may be a porous structure having a plurality of through pores.

In the hydrocarbon sensor, a constant DC voltage source and an amperemeter are connected in series through proper leads to the anode and cathode of the sensor. In measuring in an atmosphere, hydrocarbon in the atmosphere diffuses and moves through the diffusion rate determining hole, and then reaches the anode under the application of a potential difference across the anode and the cathode. At the anode, the hydrocarbon is dissociated into protons by electrolysis. The protons are conducted through the proton-conductive solid electrolyte, and reaches the cathode at which to be discharged as hydrogen. At this time, current flows across the anode and the cathode between which a constant voltage is applied in accordance with the movement amount of the protons, and limiting current is generated in proportion to the amount of hydrocarbon (i.e. the concentration of hydrocarbon in the atmosphere) subjected to diffusion rate determination in accordance with the atmosphere.

The sensor is heated to a temperature to the extent that the solid-electrolytic layer can make full use of its proton conductivity. An electric heater may be secured to the sensor itself in order to heat the sensor and control the temperature thereof.

Generally speaking, the maximum operation temperature of the sensor is determined by the heat resistance of the electrodes. Although the sensor can operate in the temperature range of 200 to 1000° C., an operation temperature of 300° C. or more is desirable to oxidize the surface of the Al-containing metal layer used as the cathode. In particular, the temperature range of 300 to 800° C. is desirable.

EXAMPLE 1

FIG. 1 shows the structure of a current-detection type hydrocarbon sensor in accordance with the present invention. The solid electrolyte 3 of the sensor was formed of a sintered body of $BaCe_{0.8}Gd_{0.2}O_{3-\alpha}$ having a size of 10 mm×10 mm and a thickness of 0.45 mm. A cathode 4 (active electrode) made of a material mainly containing Al was formed on one side of a thin film of a sintered body, i.e. the solid electrolyte layer 3. On the other hand, an anode 2 (reference electrode) made of platinum was formed on the other side.

To obtain a material mainly containing Al for the Al-containing metal layer on the cathode side, a mixture of 5% by weight of Si powder and 1 to 2% by weight of silica powder and the balance Al powder were blended with liquid thermosetting resin, preparing paste. This paste was applied in a form of film on one side of the solid electrolyte 3 in accordance with a desired pattern by screen printing, and the film was baked at 850° C. to form the Al-containing metal layer. At the same time, the other electrode, the anode made of platinum (Pt), was made by applying paste including platinum powder to the other side by screen printing and by baking the paste.

A preliminary experiment was conducted to evaluate this prototype sensor. The voltage-current characteristic (in accordance with the potential step method) was examined in butane containing gas (1% butane) and in the air at 600° C. The results are shown in FIG. 2.

In the case of a sensor having two electrodes both made of platinum, output current presumably caused owing to oxygen ion conduction flows in the air in both cases of anodic voltage application (to the reference electrode) and cathodic voltage application. The output current characteristic is symmetrical with respect to the 0 V point.

Figure 2:
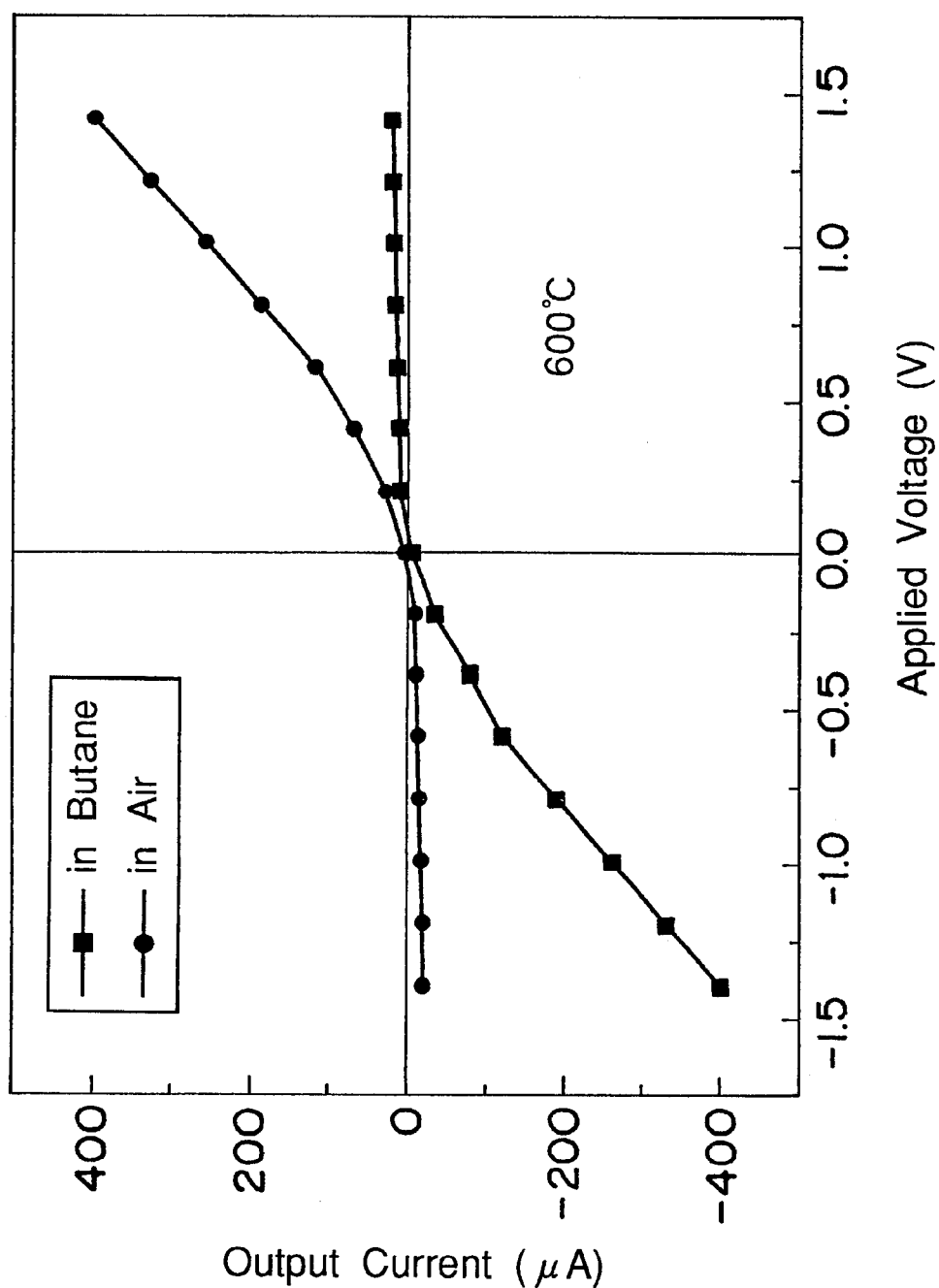
FIG. 2 is a graph showing voltage-current characteristics of the hydrocarbon sensor of the present invention.

On the other hand, in the case of a sensor having an Al-containing metal electrode, current hardly flows in the air, but current flows in butane gas presumably owing to proton conduction as shown in FIG. 2 (because the Ba—Ce-based oxide is a mixing ion conductor for both protons and oxide ions). In other words, it is assumed that oxygen is blocked by the Al electrode in the air (in the presence of oxygen), and that proton conduction is caused in hydrocarbon by cathodic voltage application. By using this principle, it is possible to attain a hydrocarbon sensor capable of operating properly regardless of the existence or absence of oxygen.

Figure 3:
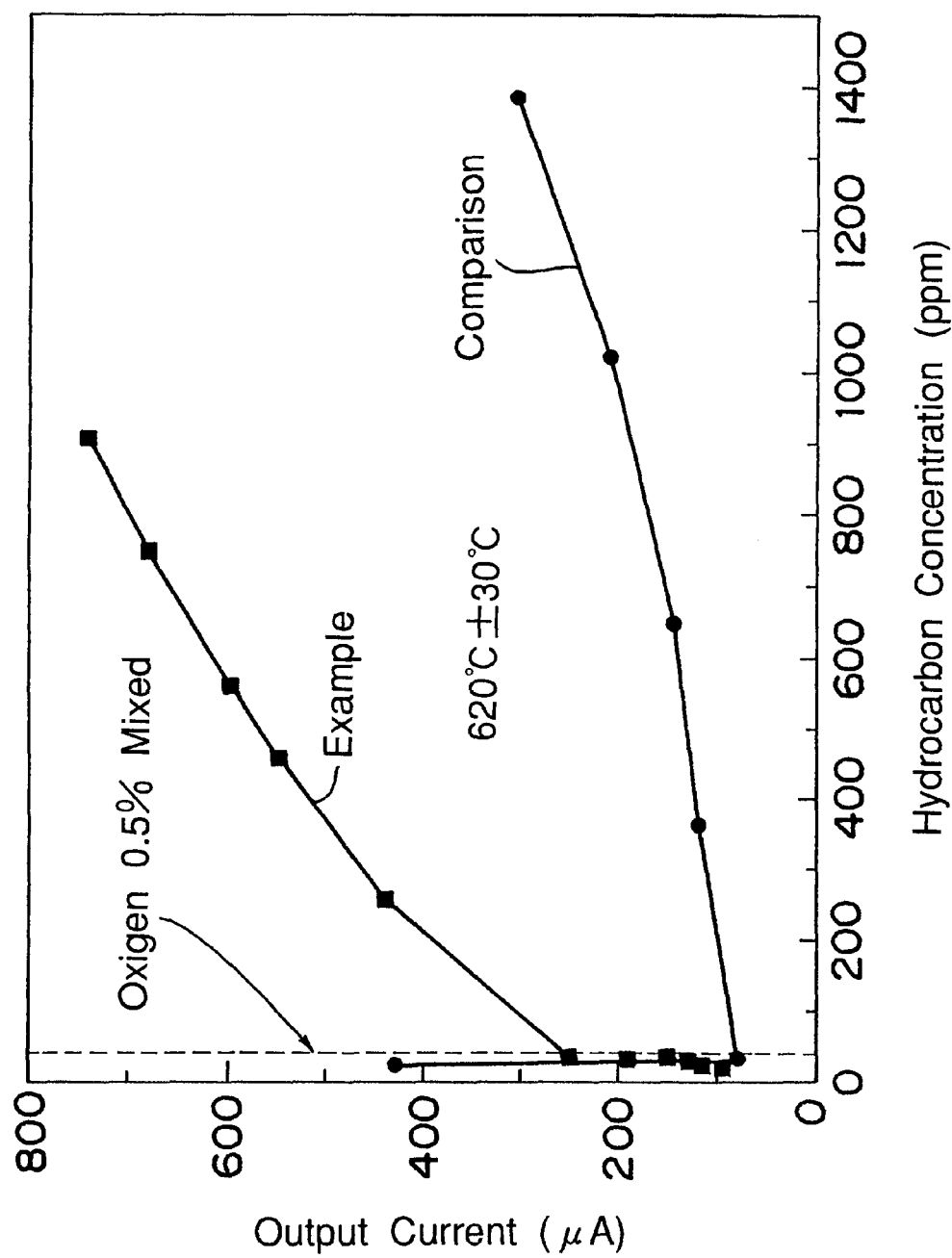
FIG. 3 is a graph showing the relationship between concentration of hydrocarbon in an atmosphere and output current of the hydrocarbon sensor in accordance with the example of the present invention.

Next, this sensor was checked actually to determine whether the sensor functions properly as a hydrocarbon sensor by using an actual vehicle engine. The temperature of the device was maintained at about 600° C. A voltage of 1.2 V was applied so that the Al electrode becomes negative, and the output of the device was examined at various hydrocarbon concentrations. FIG. 3 shows the relationship between hydrocarbon concentration and output. In addition, the output characteristic of the conventional sensor having two electrodes made of platinum is also shown for comparison. In the case of the conventional sensor, its output increased abruptly as shown in FIG. 3 when the entry of oxygen occurred at low hydrocarbon concentrations. In the case of the sensor of the present invention, however, it is found that its output remains low. This obviously indicates that the sensor of the present invention detects only hydrocarbon stablly, without being affected by the entry of oxygen in the atmosphere to the sensor.

Figure 4:
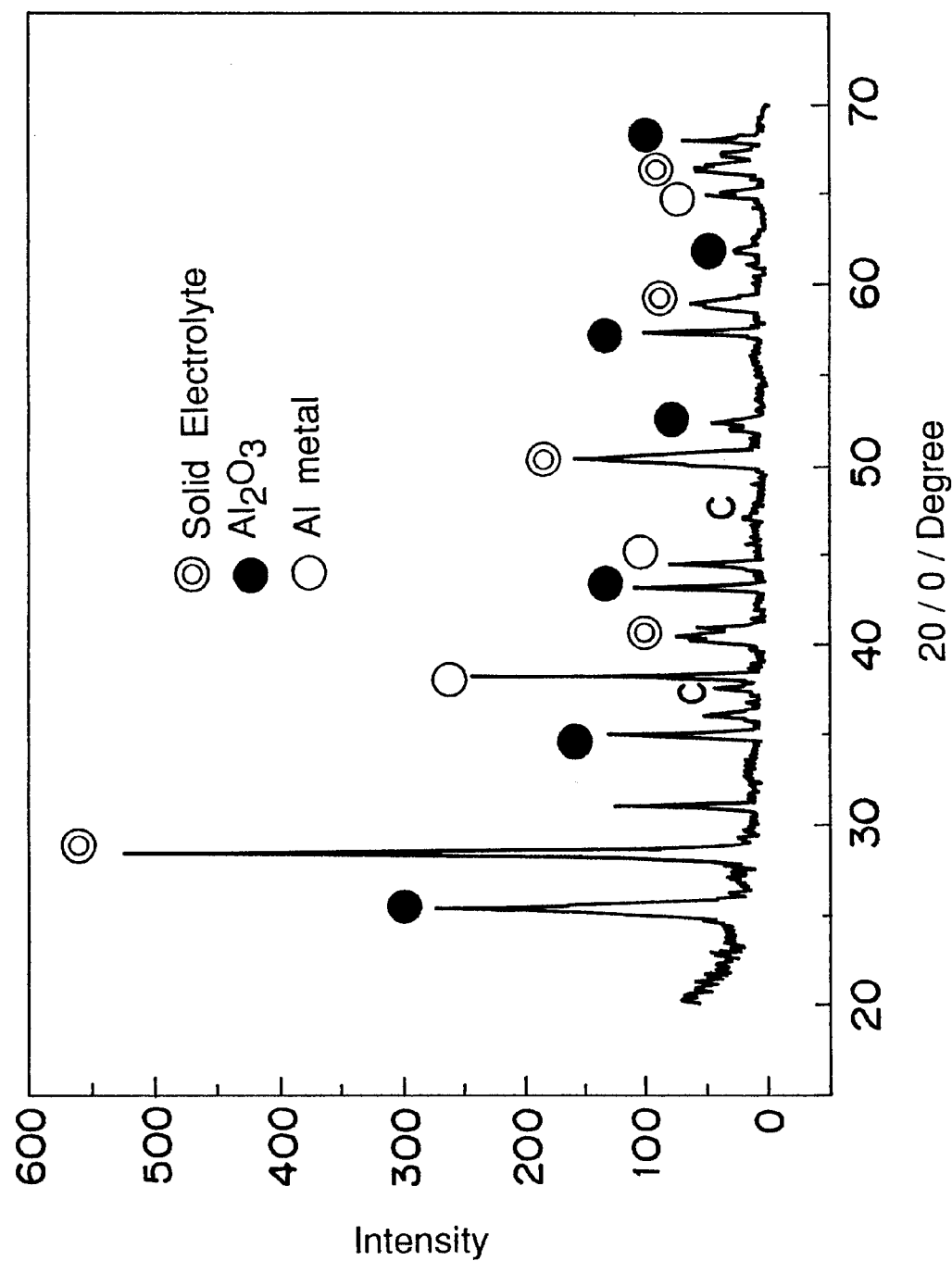
FIG. 4 is a chart showing the X-ray diffraction intensity on a surface of an Al electrode used as an anode of the hydrocarbon sensor of the present invention.

The reaction mechanism and principle of the sensor of the present invention will be considered by supposition as follows. FIG. 4 shows the X-ray diffraction pattern of the Al electrode disposed on the electrolyte 3. It is found from the diffraction pattern that part of the Al electrode is oxidized.

Figure 5:
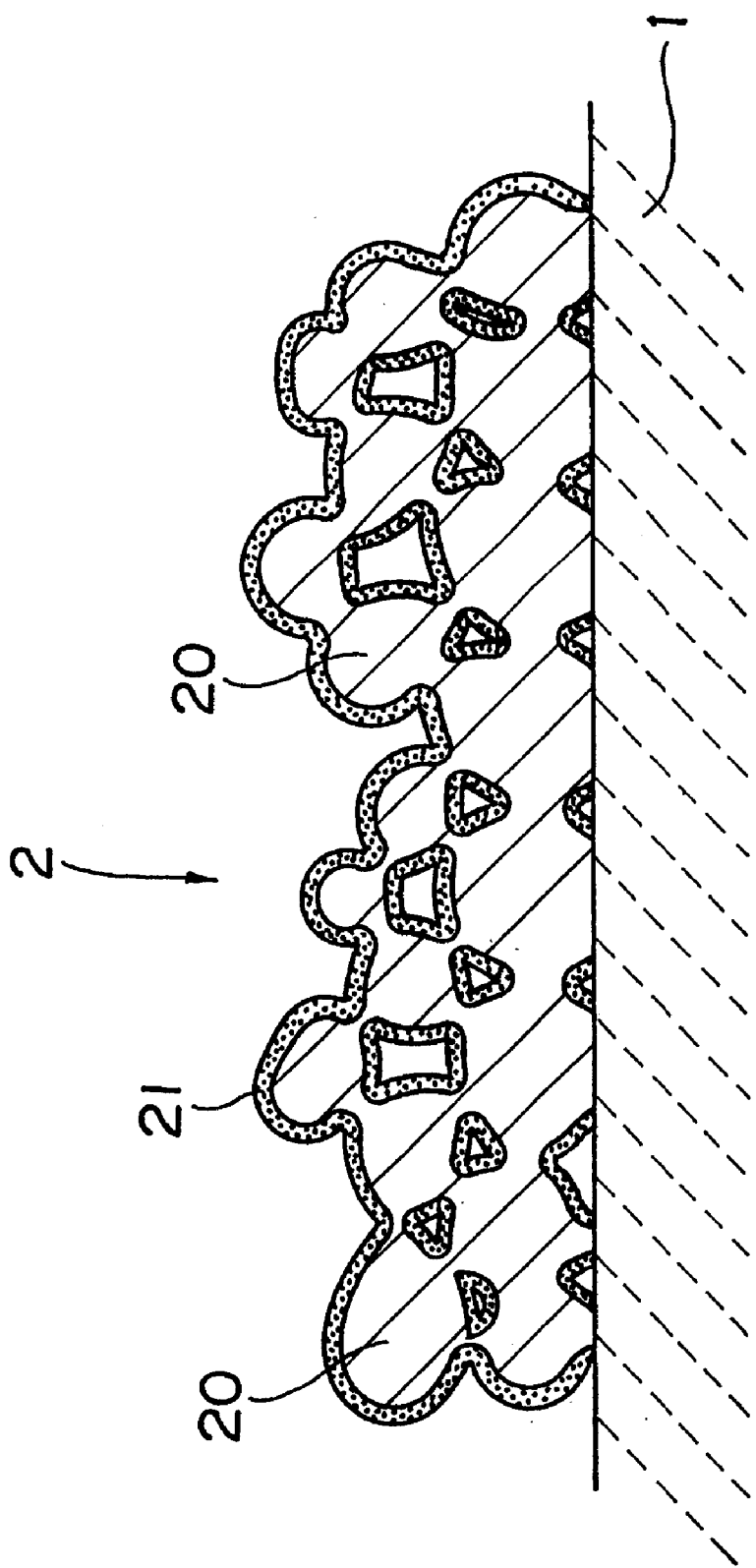
FIG. 5 is a schematic sectional view showing the structure of an Al electrode used as an anode of the hydrocarbon sensor of the present invention.

If the entire Al electrode is oxidized, the electrode becomes a nonconductor, and it is thus assumed that the electrode does not function as an electrode. However, conduction occurs depending on the polarity of the applied voltage and the kind of the gas in an atmosphere as described above. In consideration of this, it is assumed that an Al metal 20 remains unchanged inside the Al electrode, and that an oxidized film 21 (anodized aluminum layer) is formed on the surface of the metal, as schematically shown in FIG. 5. Accordingly, even if the temperature rises to the melting point of the Al metal, 660° C., or more during operation, it is assumed that the oxidized film 21 prevents the Al metal 20 from fusing and condensing.

EXAMPLE 2

The present example is a hydrocarbon sensor comprising a pair of electrodes and a solid electrolyte 3 made of a Ba—Ce-based oxide and having a hydrocarbon diffusion rate determining layer, wherein the cathode thereof is made of a material mainly containing Al. In this example, an aluminum oxide layer is formed on the surface of the cathode made of Al.

Figure 6:
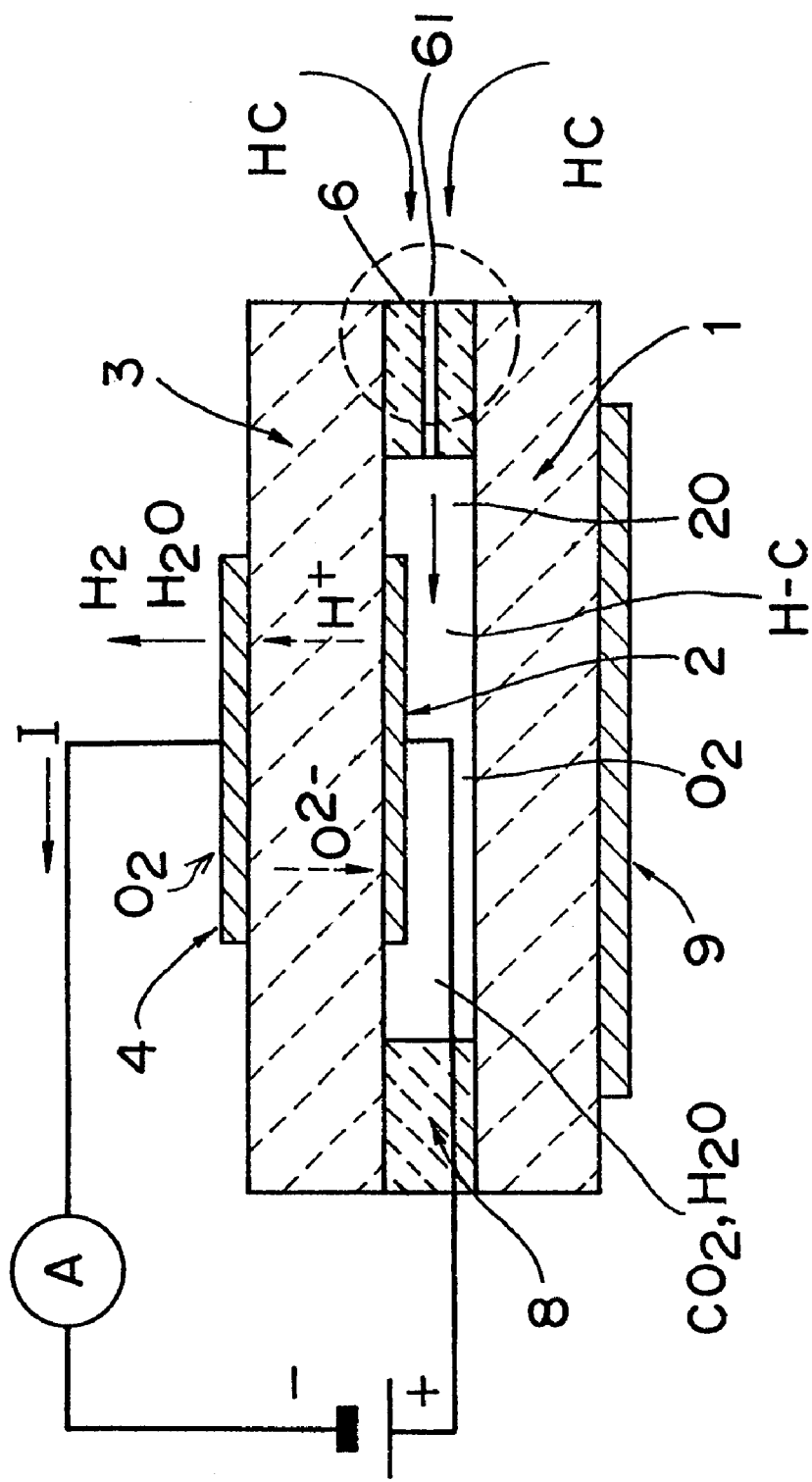
FIG. 6 is a schematic sectional view showing a limiting-current type hydrocarbon sensor in accordance with an example of the present invention.

FIG. 6 shows the structure of the limiting-current type hydrocarbon sensor of the present invention. The solid electrolyte 3 of the sensor was formed of a sintered body of $BaCe_{0.8}Y_{0.2}O_{3-\alpha}$ having a size of 10 mm×10 mm and a thickness of 0.45 mm. An anode 2 was made of platinum, and a cathode 4 was formed of an Al-containing metal layer. In this example, to obtain a material mainly containing Al for the Al-containing metal layer, Al powder, 0.1% of Cu powder, 2% of Si powder and 2% of $SiO_2$ powder were mixed, and paste was thus prepared. This paste was applied on the solid electrolyte 3 by screen printing, and baked at 900° C. to obtain a sintered electrode.

On the anode side of the solid-electrolytic layer 3 of the sensor, a diffusion rate determining layer was formed as described below. Only the peripheral portion of a ceramic substrate 1 was adhered to the surface of the solid-electrolytic layer 3 on the anode side via an inorganic adhesive 6 so as to cover over the anode 2, thereby forming an anode chamber 20, and a diffusion rate determining hole 61 communicating to an atmosphere was then formed between the ceramic substrate 1 and the solid-electrolytic layer 3. The sensor was further provided with a heater 9 on the outside of the ceramic substrate 1 so as to be heated to a predetermined temperature. In this way, a proton-conductive limiting-current type hydrocarbon sensor was formed.

Figure 7:
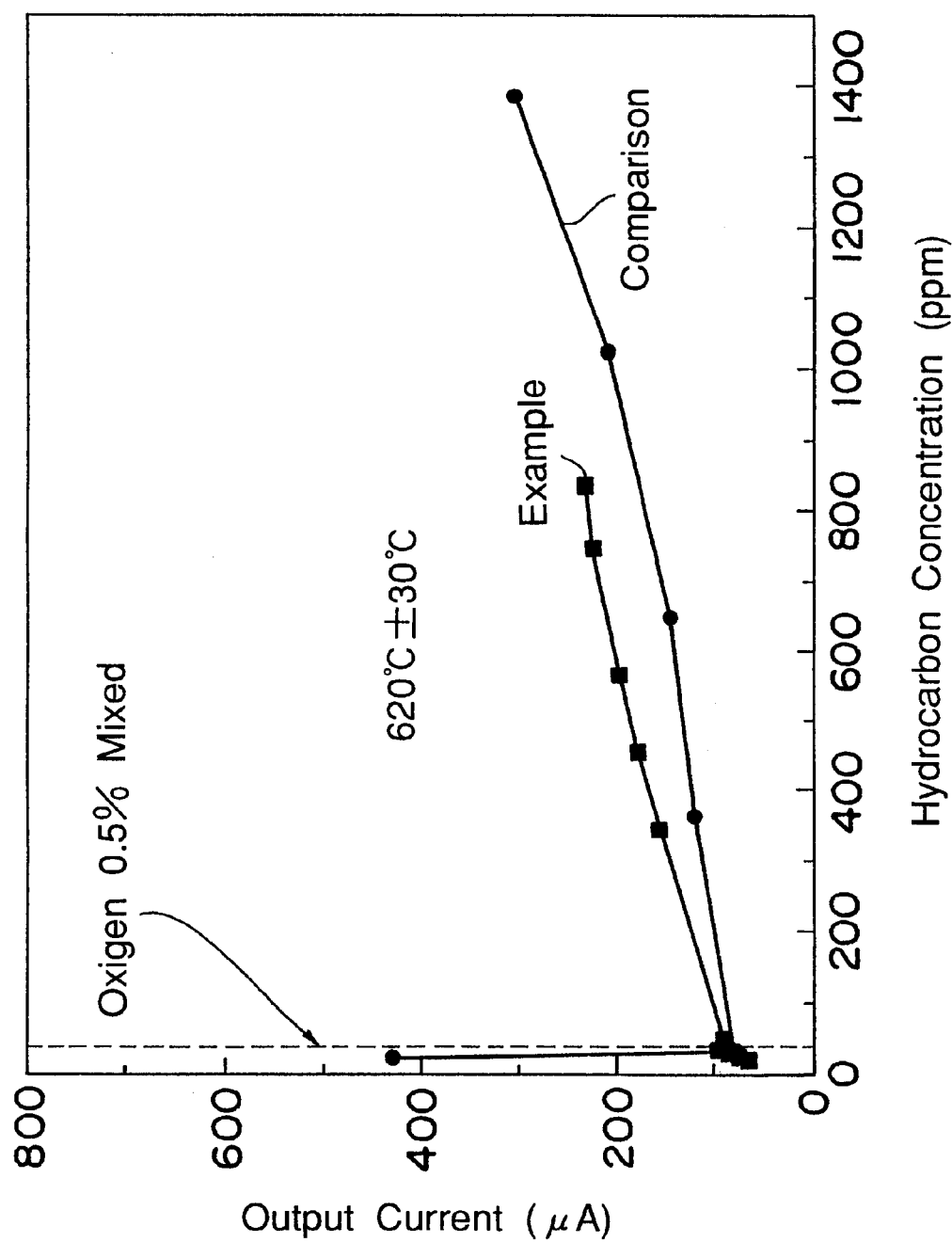
FIG. 7 is a graph showing the relationship between concentration of hydrocarbon and output current of the limiting-current type hydrocarbon sensor in accordance with the example of the present invention.

Just as in the case of the above-mentioned example 1, the detection characteristic of this sensor was examined by using vehicle exhaust as gas to be detected. The temperature of the device was maintained at about 600° C. A voltage of 1.2 V was applied, and the output current of the device was examined at various gas concentrations. FIG. 7 shows the relationship between hydrocarbon concentration and output of current. In addition, in this FIG. 7 the output characteristic of the conventional sensor having an anode and a cathode both made of platinum is also shown for comparison.

In the case of the conventional sensor, as shown in FIG. 7, its output current increased abruptly when the entry of oxygen to the atmosphere occurred at low hydrocarbon concentrations. In the sensor of the present invention, however, it is found that the output current was not changed even by the entry of oxygen to the atmosphere, and that the output is stable. This obviously indicates that the sensor of the present invention can stably detect hydrocarbon even at the time of the entry of oxygen. It is therefore assumed that the surface of the electrode mainly containing Al in this sensor is coated with an oxidized film, and that the entry of oxygen from the cathode is blocked in the same manner just as in the case of Example 1.

As obviously indicated by the detection results of the present example, it is found that the hydrocarbon sensor comprising a solid-electrolytic layer made of a Ba—Ce-based oxide and a cathode made of a material mainly containing Al can stably detect hydrocarbon, whether in the presence or absence of oxygen. Furthermore, it is also indicated that the characteristic of the sensor is not affected by the existence of oxygen, provided that the sensor is structured so as to be provided with a cathode made of Al, on the surface of which an aluminum oxide layer is formed.

EXAMPLE 3

The present example is a hydrocarbon sensor comprising a pair of electrodes and a solid electrolyte 3 made of a Ba—Ce-based oxide and having a hydrocarbon diffusion rate determining layer, wherein its anode is made of a material mainly containing Ag.

The solid electrolytic layer 3 of the sensor was formed of a sintered body of $BaCe_{0.8}Gd_{0.2}O_{3-\alpha}$ having an external size of 10 mm×10 mm and a thickness of 0.45 mm. On the surfaces of a solid electrolytic layer 3, an anode 2 made of Ag was formed, and a cathode 4 made of an Al-containing material mainly containing Al was also formed as shown in FIG. 6. Each electrode material was formed into paste, and applied onto the solid electrolyte 3 by screen printing to form a film. After drying, the film was baked at 850° C. to obtain a sintered electrode.

Furthermore, the solid electrolytic layer 3 on the side of the anode 2 was covered with a ceramic substrate 1 via an inorganic adhesive 8 to form a hydrocarbon diffusion rate determining hole, and a resistance-heating type heater 9 was secured to the outer surface of the ceramic substrate 1, thereby forming a limiting-current type sensor.

In the same conditions as those in the case of the example 2, the characteristic of this sensor was examined by using vehicle exhaust as gas to be detected. The temperature of the sensor was heated to 600° C. in the exhaust, a voltage of 1.2 V was applied across the electrodes, and the characteristic of the device was examined.

Figure 8:
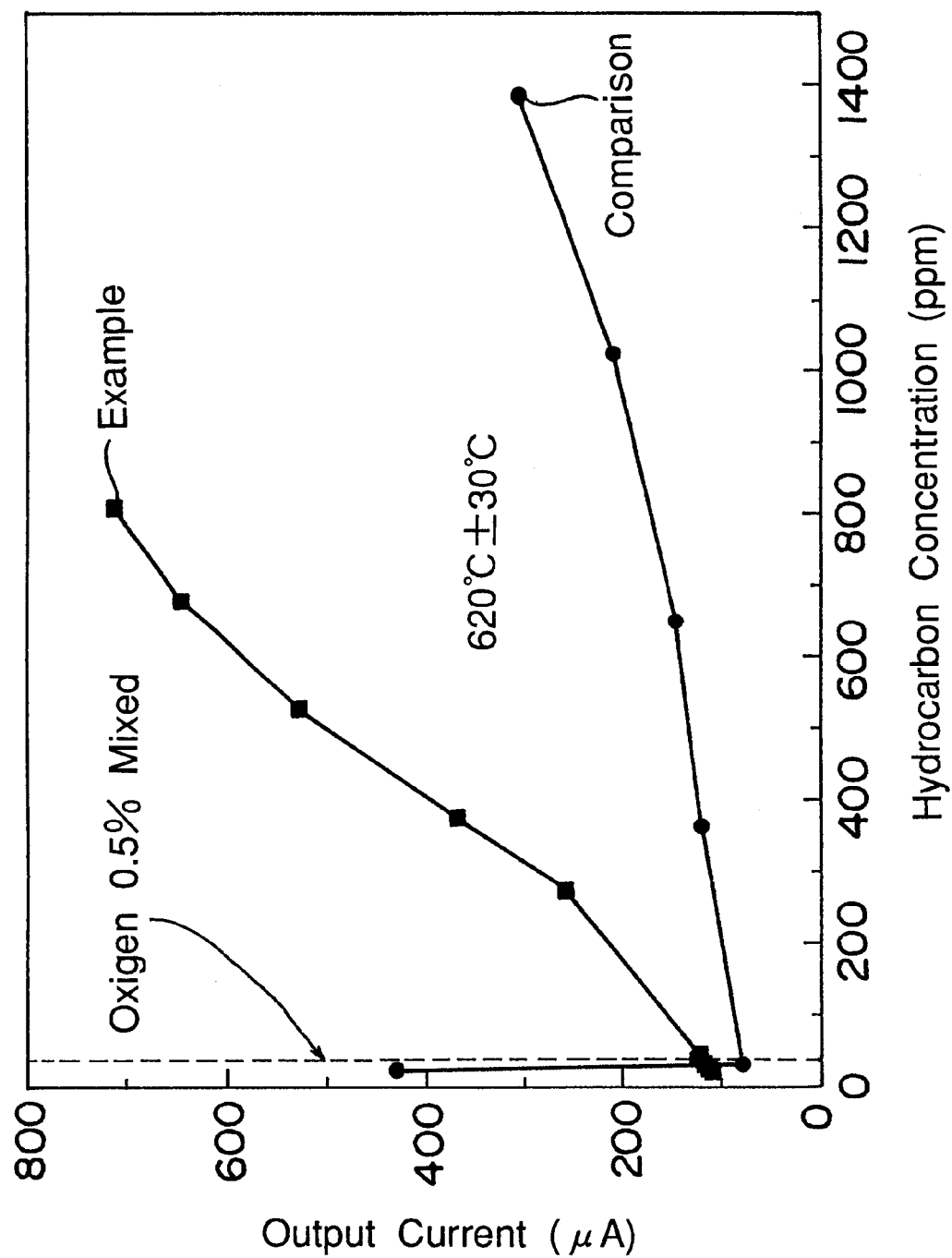
FIG. 8 is a graph showing the relationship between the concentration of hydrocarbon and the output current of the limiting-current type hydrocarbon sensor in accordance with another example of the present invention.

FIG. 8 shows the relationship between hydrocarbon concentration and output current in the sensor of this example. In addition, in this FIG. 8, the output characteristic of a conventional sensor having an anode made of Pt and an cathode made of Al, the areas of the anode and cathode being the same as those of the present example, is also shown for comparison. As a result, it is found that the output of the sensor of the present invention is about 10 times as high as the output, i.e. sensitivity, of the conventional sensor. As described above, by using the anode made of a material mainly containing Ag as an electrode disposed opposite to the cathode made of Al, the sensor can detect hydrocarbon at high sensitivity and high accuracy.

As a second kind of sensor, a hydrocarbon sensor provided with an ion pump in accordance with the present invention will be described below. This hydrocarbon sensor is applicable to a limiting-current type sensor and an EMF-type sensor.

Figure 9A:
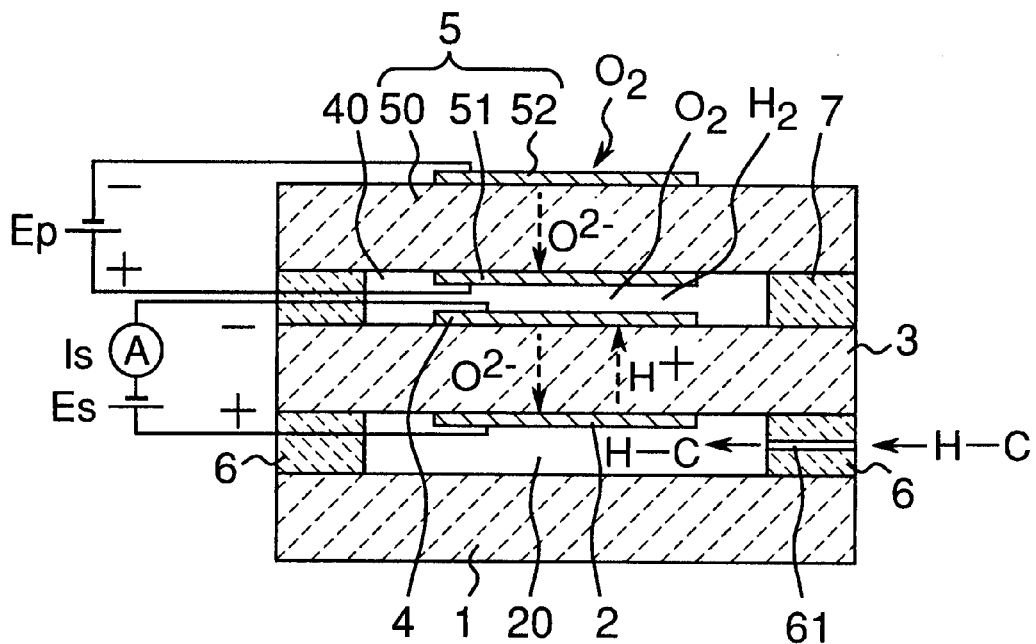
FIGS. 9A and 9B are schematic sectional views showing a limiting-current type hydrocarbon sensor of the present invention.

The sectional structure of a limiting-current type hydrocarbon sensor is shown in FIG. 9A. A thin sensor-use solid-electrolytic layer 3, on one side of which a cathode 4 is mounted and on the other side of which an anode 2 is mounted, is secured onto a ceramic substrate 1. A gas diffusion rate determining portion is formed on the surface of the solid-electrolytic layer 3 on the side of the anode 2.

The gas diffusion rate determining portion is supported via a spacer at the peripheral portion thereof 6 between the anode 2 and the substrate 1, and comprises a hermetically sealed anode chamber 20 and a small-diameter diffusion hole 61 for communicating the anode chamber 20 to the outside of the sensor. In the case of this example, the diffusion hole 61 is a single small hole passing through part of the insulating spacer. The diffusion hole is not limited to such a single small hole. Porous through holes can also be used.

The solid-electrolytic layer 3 of the sensor of the present invention is made of a proton-oxide ion conductor, such as a $BaCeO_{3-\alpha}$-based oxide, and the anode 2 and the cathode 4 are made of an active metal having high corrosion resistance, such as Pt, Au or Pd.

In the present invention, a solid ion pump 5 is formed of a thin solid-electrolytic layer 50 for use in ion pump, on both sides of which pump electrodes 51 and 52 are mounted securely, one electrode on each side. The pump-use solid-electrolytic layer 50 is disposed on the sensor-use solid-electrolytic layer 3 on the side of the cathode 4 with a space 40 provided therebetween. Furthermore, the two solid-electrolytic layers 3, 50 are adhered to each other and supported via an insulating spacer 7, i.e., inorganic adhesive, provided therebetween at the peripheral portions thereof. The space is hermetically sealed so as to be used as a cathode chamber 40.

A constant-voltage system and a constant-current system for driving the ion pump can be used to supply electricity to the two electrodes on the pump-use solid-electrolytic layer. In the constant-voltage system, a constant voltage is applied across the pump-use electrodes on the solid-electrolytic layer so that the gas components such as oxygen, hydrogen or water on the outside atmosphere or inside of the cathode chamber can be passed through the solid-electrolytic layer towards the opposite side then transferring in accordance with the partial pressure of the gas components.

Furthermore, in the case of the constant-current system, a constant current is supplied across both pump-use electrodes so that the gas components such as oxygen, etc, in the outside atmosphere or in the inside of cathode chamber can be passed through the solid-electrolytic layer and pumped at a flow rate of the ions in accordance with the electric current. As a result, the concentration of the oxygen in the cathode chamber can be controlled without being affected by the concentration of the gas components in the outside. For this reason, the hydrocarbon sensor can be free from the dependence of its characteristic on the concentration of the oxygen. In this way, the constant-current system is advantageous in that the concentration of hydrocarbon can be detected and measured highly accurately.

A hydrocarbon sensor in accordance with a first embodiment of the present invention is a sensor for transferring an approximately constant amount of oxygen in an atmosphere under measurement to its cathode chamber by using a solid ion pump formed of an oxide ion conductor.

In the oxygen pump of this sensor of this first embodiment, as shown in FIG. 9A, the inner electrode 51 on the cathode chamber side is used as a positive electrode, and the outer electrode 52 is used as a negative electrode. A constant voltage or constant current is applied across the inner and outer electrodes to flow current through the pump-use solid-electrolytic layer 50, thereby to pass exter-nal oxygen through the solid-electrolytic layer and to move a constant amount of oxygen into the cathode chamber. The movement amount of the oxygen is controlled depending on current. In this process, a constant amount of oxygen in the cathode chamber decomposes at the cathode regardless of the concentration of the oxygen in an external atmosphere. As a result, the output of the oxygen ion current becomes constant owing to the stabile partial pressure of the oxygen in the cathode chamber, and an output corresponding to only the change in hydrocarbon can be obtained as the output of the sensor.

The solid-electrolytic layer for this pump is formed of an oxide ion conductor for mainly transferring oxygen. This kind of ion conductor may be made of an oxide including at least one element selected from among Zr, Ce, Bi, Ca, Ba and Sr.

This kind of solid-electrolytic layer may preferably be formed of a sintered body of zirconia including 8% of Y, bismuth oxides, cerium oxides or the like. Anything can be used as long as it is an oxide ion conductor.

The inner electrode 51 and the outer electrode 52 are formed of a corrosion-resistant active metal. For example, a metal, such as Rt, Au or Pd, is preferably used in the form of a thin film.

Figure 9B:
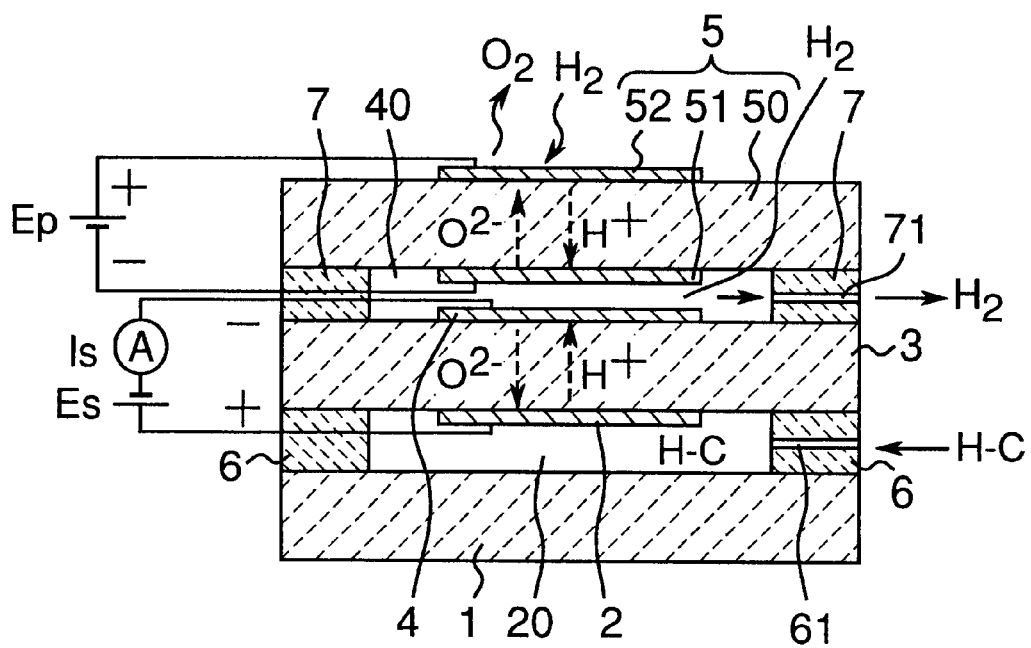

A second embodiment is a hydrocarbon sensor comprising a solid ion pump 5 for pumping the oxygen inside the cathode chamber 40 into an atmosphere. In this case, as shown in FIG. 9B, polarity of the electrodes on the pump-use solid-electrolytic layer 50 thereof are opposite to those in the first embodiment. In other words, the inner electrode 51 on the side of the cathode chamber 40 is used as a negative electrode, the outer electrode is used as a positive electrode, and current is applied across the electrodes. The solid ion pump is driven in the direction for pumping the oxygen from the inside of the cathode chamber 40 to the outside. The partial pressure of the oxygen in the cathode chamber is thus lowered so as not to supply oxygen to the cathode 4 of the sensor, thereby eliminating the effect of the oxygen in the atmosphere on the output of the hydrocarbon sensor. The solid-electrolytic layer for used in this pump is formed of an oxide ion conductor for transferring oxygen just as in the case of the first embodiment.

In this sensor in accordance with the second embodiment, protons passed through the electrolytic layer and moved from the anode 2 to the cathode 4 generate hydrogen in the cathode chamber 40, and the hydrogen stays therein. A small-diameter vent hole 71 should preferably be formed in a spacer 7 disposed between the pump-use solid-electrolytic layer 50 and the sensor-use electrolytic layer 3 as shown in FIG. 9B to communicate the cathode chamber 40 to the atmosphere. This vent hole 71 should preferably have a small diameter to the extent that the diffusion and entry of hydrogen are carried out easily but those of oxygen are limited.

Figure 10:
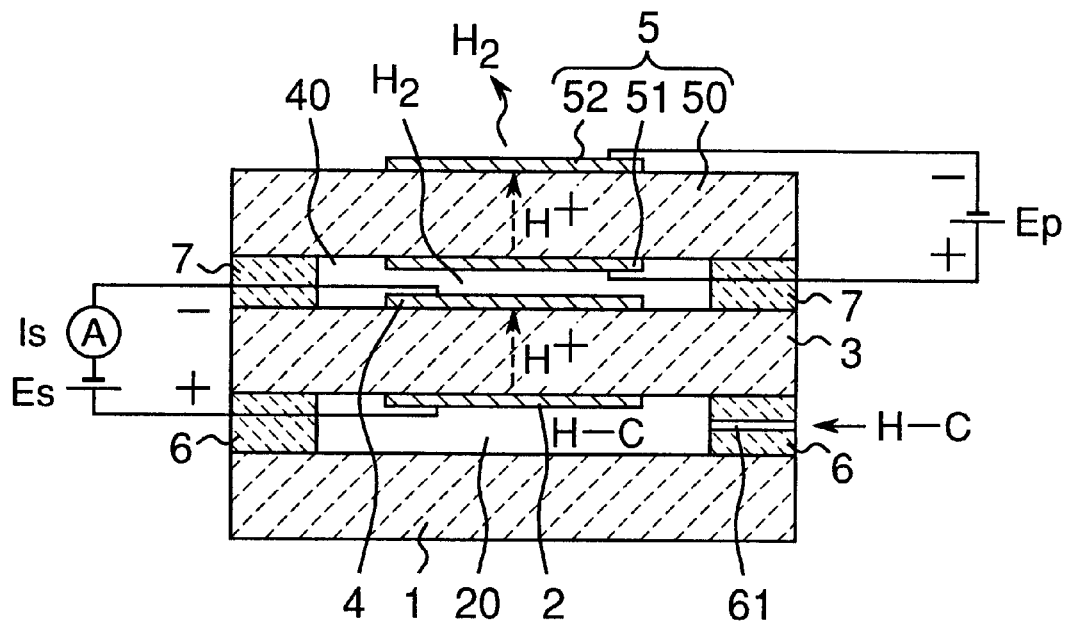
FIG. 10 is a schematic sectional view showing another limiting-current type hydrocarbon sensor of the present invention.

A third embodiment is a hydrocarbon sensor comprising a solid ion pump formed of a proton conductor for transferring hydrogen or water vapor. In the pump-use solid-electrolytic layer in accordance with this embodiment, as shown in FIG. 10, the inner electrode 51 on the cathode chamber side 40 is used as a positive electrode, and the outer electrode 52 is used as a negative electrode. A constant voltage or constant current is applied across the inner and outer electrodes. Hydrogen or its compound, i.e. water vapor, generated at the cathode 4 of the sensor is passed through the pump-use solid-electrolytic layer 50 and can be discharged outside. Since the solid-electrolytic layer 50 is formed of a proton conductor, the entry of oxygen is limited, and the partial pressure of oxygen in the cathode chamber can be reduced. As a result, an output corresponding to only the change in hydrocarbon can be obtained as the output of the sensor, regardless of the concentration of oxygen in an atmosphere.

The solid-electrolytic layer for this pump is formed of a proton conductor for transferring hydrogen. The proton conductor is made of an oxide including at least one element selected from among Zr, Ce, Bi, Ca, Ba and Sr. The solid-electrolytic layer for the pump may be formed of any type of proton conductor as long as it has a composition of $SrCe_{0.9}Gd_{0.1}O_{3-\alpha}$ or $CaZr_{0.9}In_{0.1}O_{3-\alpha}$. In particular, the proton conductor should have high conductivity for protons and low conductivity for oxides.

A fourth embodiment is a hydrocarbon sensor comprising a pump-use solid-electrolytic layer for transferring oxygen and hydrogen simultaneously. The pump-use solid-electrolytic layer is therefore formed of an oxide ion-proton conductor. In particular, the pump-use solid-electrolytic layer is made of an oxide including at least Ba and Ce, i.e. $BaCeO_{3-\alpha}$.

Figure 11:
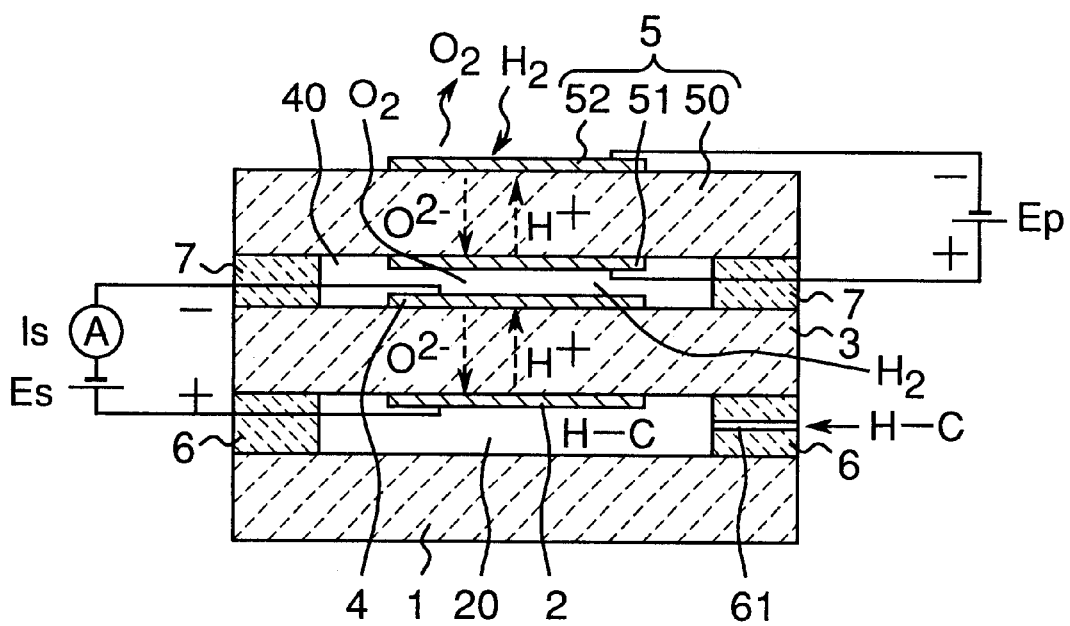
FIG. 11 is a schematic sectional view showing still another limiting-current type hydrocarbon sensor of the present invention.

In this fourth embodiment, the solid ion pump functions as an oxygen-hydrogen pump. As shown in FIG. 11, the inner electrode 51 of the pump-use solid-electrolytic layer 50 on the side of the cathode chamber 40 is used as a positive electrode, and the outer electrode 52 thereof is used as a negative electrode. A constant voltage or current is applied across the inner and outer electrodes. By this application, external oxygen is passed through the pump-use solid-electrolytic layer 50 and moved to the cathode chamber 40 at a constant rate. At the same time, hydrogen generated in the cathode chamber 40 is passed through the solid-electrolytic layer 50 and transferred to an external atmosphere. As a result, the output of the hydrocarbon sensor becomes a constant oxygen ion current due to the nearly constant partial pressure of oxygen at the cathode chamber, regardless of the concentration of oxygen in the external atmosphere. Therefore, an output corresponding to only the change in hydrocarbon can be obtained as the output of the sensor.

Even in the system of supplying electricity to the solid-electrolytic layer for the oxygen-hydrogen pump, a constant voltage system and a constant current system are used.

In the constant voltage system, hydrogen and water vapor accumulated in the cathode chamber are passed through the solid-electrolytic layer and discharged outside, while a constant amount of external oxygen is moved to the cathode chamber at the same time. The decomposition of oxygen occurs in the cathode chamber at a constant rate, regardless of external oxygen. As a result, an output corresponding to only the hydrocarbon can be obtained as the output of the sensor.

On the other hand, in the case of the constant current system, the total movement amount of gas ion passing through the solid-electrolytic layer is controlled so as to be constant. For this reason, the amount of pumping can be controlled depending on the amount of the gas generated from the cathode chamber of solid-electrolytic layer of the sensor. As a result, the concentration in the cathode chamber can be controlled easily, and hydrocarbon can be detected at high accuracy.

The cathode formed of the above-mentioned Al-containing metal layer is used for a limiting-current type hydrocarbon sensor comprising an ion pump formed on the cathode side. This kind of sensor has more significant insensitivity to oxygen owing to the combined use of the ion pump on the cathode side and the cathode formed of the Al-containing metal layer. For this reason, hydrocarbon measurement errors due to oxygen in an atmosphere can be eliminated from the sensor.

Next, an example is shown wherein the sensor comprising the ion pump of the present invention is applied so as to be used as an EMF-type hydrocarbon sensor.

Figure 12:
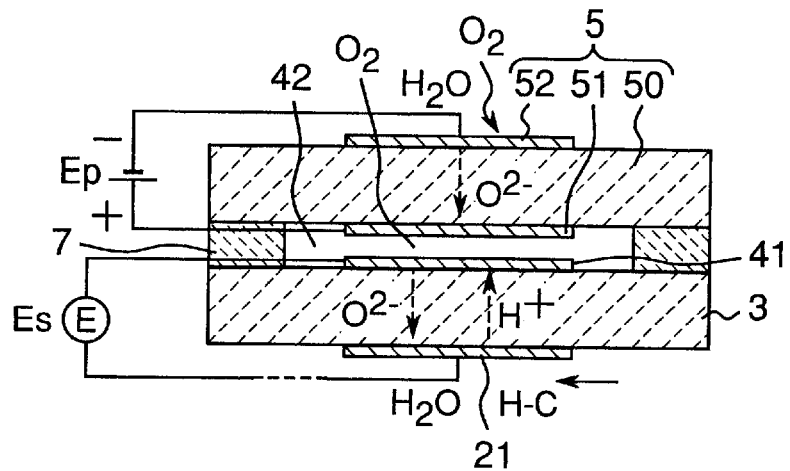
FIG. 12 is a schematic sectional view showing an EMF-type hydrocarbon sensor of the present invention.

As a fifth embodiment, a hydrocarbon sensor is shown in a shematic view of FIG. 12. On the two main surfaces of the sensor-use solid-electrolytic layer 3, a hydrocarbon active electrode 21 and a standard electrode 41 are formed. The hydrocarbon active electrode 21 is directly exposed to an atmosphere under measurement.

The solid ion pump of the present invention is mounted on the other electrode, i.e. the standard electrode 41, and the standard electrode 41 is exposed to a standard electrode chamber 42. The solid ion pump comprises a thin solid-electrolytic layer 50 and pump-use electrodes 51, 52 secured to both sides of the layer, one electrode on each side. The pump-use electrolytic layer 50 is mounted on the surface of the sensor-use solid-electrolytic layer 3 on the standard electrode side so that the two electrolytic layers 50, 3 are adhered to each other at their peripheral portions via an insulating spacer 7 with a space 42 provided therebetween. The space is hermetically sealed and used as a standard electrode chamber 42.

In the EMF-type sensor, the solid ion pump is operated as an oxygen pump. Current is flown in the direction of supplying oxygen to the sensor device (the outer electrode 52 is used as a negative electrode, and the inner electrode 51 is used as a positive electrode). Oxygen is passed from an atmosphere through the sensor-use solid-electrolytic layer 50, and the oxygen polarization potential of the inactive electrode 41 is used as a reference electrode potential.

At the time of measurement, this EMF-type sensor is placed in an atmosphere under measurement. Protons are generated by the decomposition of hydrocarbon at the hydrocarbon active electrode exposed to the atmosphere at this time, and oxygen ions are generated at the standard electrode (inactive electrode). As a result, a cell electromotive force is generated by an oxygen-hydrogen oxidation-reduction reaction between the active electrode 21 and the inactive electrode 41. The concentration of hydrocarbon in the atmosphere can be detected by measuring the electromotive force across the two electrodes. This hydrocarbon sensor provides a larger electromotive force and higher sensitivity than a conventional hydrogen-hydrogen concentration cell type hydrocarbon sensor at the same concentration of hydrocarbon. In addition, in an atmosphere in which the entry of oxygen occurs, this hydrocarbon sensor is characterized that its cell electromotive force lowers, unlike the conventional cell type.

The pump-use solid-electrolytic layer of the EMF-type sensor is formed of an oxide ion conductor made of an oxide including at least one element selected from among Zr, Ce, Bi, Ca, Ba and Sr in particular. Furthermore, the sensor-use solid-electrolytic layer is made of an oxide for conducting protons and oxide ions simultaneously, selected from among oxides including at least Ba and Ce.

More specifically, both the pump-use and sensor-use solid-electrolytic layers can be formed of a $BaCeO_{3-\alpha}$-based ion conductor. In particular, $BaCe_{0.8}Dy_{0.2}O_{3-\alpha}$, $BaCe_{0.8}Gd_{0.2}O_{3-\alpha}$, $BaCe_{0.8}Y_{0.2}O_{3-\alpha}$, $BaCe_{0.8}Sm_{0.2}O_{3-\alpha}$, $BaCe_{0.8}Tb_{0.2}O_{3-\alpha}$ and the like can be used.

EXAMPLE 4

This example is a limiting-current type hydrocarbon sensor comprising a solid-electrolytic layer formed of an ion conductor made of a Ba—Ce-based oxide. The solid ion pump of the sensor is formed of a solid-electrolytic layer capable of transferring oxygen.

The sensor-use solid-electrolytic layer 3 of the hydrocarbon sensor is formed of a thin $BaCe_{0.8}Gd_{0.2}O_{3-\alpha}$ sintered body having a size of 10×10 mm and a thickness of 0.45 mm as shown in FIG. 9. On the surfaces of the layer, an anode 2 made of platinum and a cathode 4 also made of platinum are formed by baking, one electrode on each surface.

As shown in FIG. 9, an alumina ceramic substrate 1 is adhered by baking to the solid-electrolytic layer 3 at the outer peripheral portions thereof on the side of the anode 2 via a spacer 6 to form an anode chamber 20. The spacer 6 has a diffusion rate determining hole 61 having a small diameter to communicate the anode chamber 20 to an external atmosphere.

Furthermore, the pump-use solid-electrolytic layer 50 of the solid ion pump 5 for pumping is formed of a thin zirconia-sintered body including 8% of Y and having a size of 10×10 mm and a thickness of 0.5 mm. The electrodes 51, 52 used as a pair are each formed of a platinum film. This solid ion pump is adhered with an inorganic adhesive to the surface of the sensor-use solid-electrolytic layer 3 used as a sintered body on the side of the cathode 4 with a space provided therebetween to form a cathode chamber 40.

To examine the effect of oxygen on the sensor, a mixture gas of butane ($C_4H_{10}$) used as hydrocarbon, nitrogen and 4% water vapor was used as a gas to be measured. The concentration of oxygen was changed in the range of 0 to 2%. The sensor was placed in an electric furnace maintained at 700° C., and the output of the sensor was examined when the concentration of butane was changed in the range of 0 to 1%. The drive voltage to be applied across the electrodes 51, 52 of the pump-use solid-electrolytic layer 5 was set at a constant value of 1.0 V. The output of the sensor was observed in the movement direction of oxygen through the pump-use solid-electrolytic layer (a sintered body) to the inside of the cathode chamber and in the opposite direction, that is, the direction from the inside of the cathode chamber to an atmosphere by changing the polarity of the drive voltage.

Figure 13:
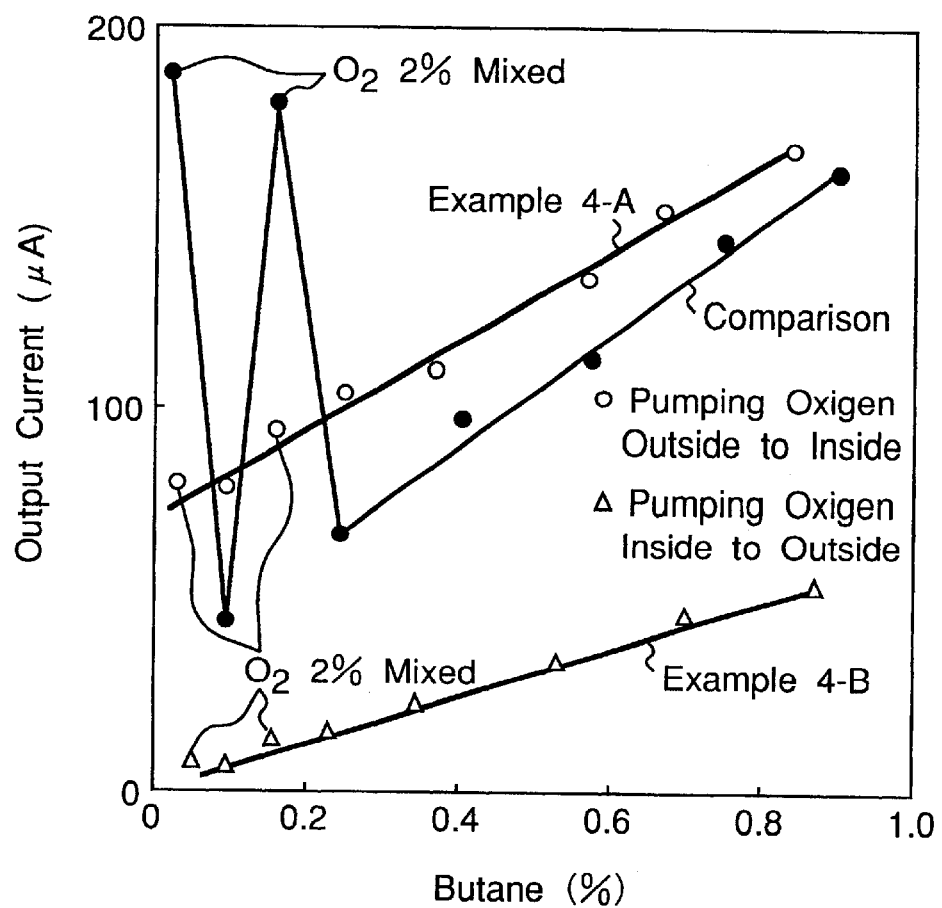
FIG. 13 is a graph showing the relationship between the concentration of butane in an atmosphere and the output current of the limiting-current type hydrocarbon sensor in accordance with another example of the present invention.

FIG. 13 is a graph showing the relationship between the concentration of butane and the output current of the sensor at the time of pump operation, and also showing the output result at the time when the sensor is not provided with the solid ion pump. Referring to this figure, in the case of the conventional example not provided with the solid ion pump, when the concentration of oxygen in an atmosphere increases by 2%, the current of the sensor increases abruptly although the concentration of hydrogen remains low. It is understood that the existence of oxygen has caused significant errors. In the case of the sensor provided with the solid ion pump, the effect of oxygen on the output of the sensor is unnoticeable despite of the change in the concentration of oxygen in the atmosphere. It is found that the output of the sensor increases linearly in proportion to the concentration of the butane gas in the atmosphere. Furthermore, it is also found that the change ratio of the current depending on the concentration of button gas is higher, and the sensitivity of the sensor is thus higher at the time when oxygen is supplied from the atmosphere to the cathode chamber than at the time when oxygen is supplied in the opposite direction. For these reasons, it is obviously found that the sensor provided with the solid ion pump in accordance with the present invention can stably detect hydrocarbon, regardless of the presence or absence of oxygen.

In the present example, the pump-use electrodes are made of platinum, and the diffusion rate determining layer is formed of a ceramic substrate and an inorganic adhesive. However, the electrodes may be made of Au or Pd instead of platinum. The diffusion rate determining layer may also be formed of a porous ceramic substrate as a matter of course. The shapes of the electrolytic layer and the electrodes are not limited in shape, forming method, etc. Furthermore, although 1.0 V is used as the voltage applied to the solid ion pump, any voltage can be applied, provided that the voltage can move gas.

EXAMPLE 5

The present example is a limiting-current type hydrocarbon sensor just as the sensor of the example 4. The solid ion pump of the sensor is formed of a solid-electrolytic layer capable of transferring hydrogen or water vapor, and the pump is used as a hydrogen pump and driven by the application of a constant voltage.

FIG. 10 shows the structure of the limiting-current type hydrocarbon sensor in accordance with the present example. The same sensor-use solid-electrolytic layer 3 (sintered body) (a sintered body of $BaCe_{0.8}Gd_{0.2}O_{3-\alpha}$ having a size of 10×10 mm and a thickness of 0.45 mm, on which an anode 2 and a cathode 4, both being made of platinum, are baked) as that of the example 4 is used. A hydrogen pump for transferring hydrogen or water vapor is formed of a sintered body of $SrCe_{0.9}Gd_{0.1}O_{3-\alpha}$ having a size of 10×10 mm and a thickness of 0.5 mm, and a pair of electrodes (an inner electrode 51 and an outer electrode 52) made of platinum.

The effect of oxygen on the output current of this sensor was examined by using a gas similar to the atmosphere. A mixture gas of butane, nitrogen and 4% water vapor was used as a gas to be measured, and the concentration of oxygen was changed in the range of 0 to 2%. The sensor was placed in an electric furnace maintained at 700° C., and the output current of the sensor was examined when the concentration of butane was changed in the range of 0 to 1%.

The drive voltage of the solid ion pump was set at a constant value of 1.0 V and applied in the direction of transferring the hydrogen or water vapor from the cathode chamber to the outside of the device. In other words, the voltage was applied across the inner electrode 51 (an electrode on the cathode chamber side and used as a positive electrode) and the outer electrode 52 (used as a negative electrode) of the pump-use solid electrolytic layer 50. The output current of the sensor was observed at this time.

Figure 14:
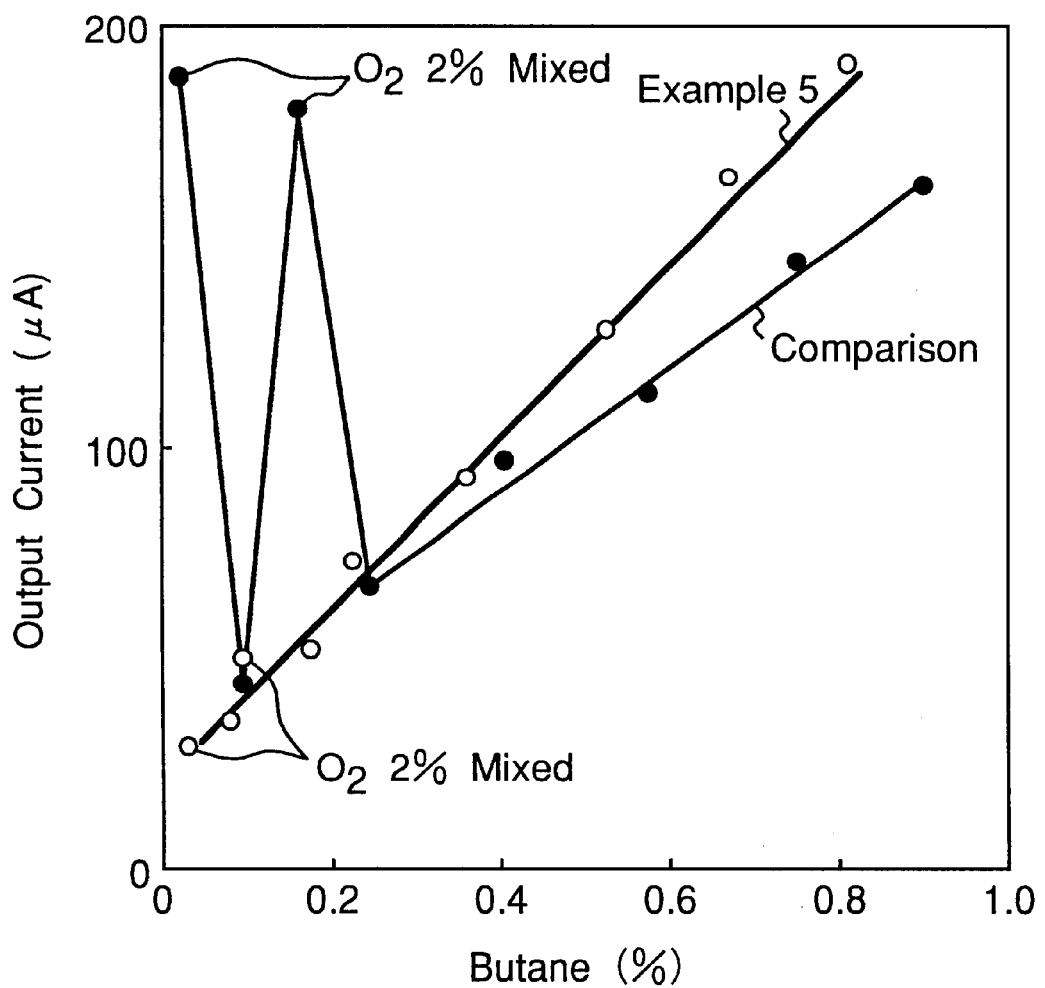
FIG. 14 is a graph showing the relationship between the concentration of butane in an atmosphere and the output current of the limiting-current type hydrocarbon sensor in accordance with another example of the present invention.

FIG. 14 shows a graph of the relationship between the concentration of butane in an atmosphere and the current output of the sensor, and also showing the output of a sensor not provided with the solid ion pump. Referring to this figure, it is found that, in the case of the sensor provided with the solid ion pump, the output of the sensor is hardly affected by the change in the concentration of oxygen in the atmosphere. For this reason, it is obviously found that the sensor provided with the solid ion pump in accordance with the present invention can stably detect hydrocarbon, regardless of the presence or absence of oxygen.

EXAMPLE 6

The present example is a limiting-current type hydrocarbon sensor comprising a solid ion pump formed of a solid-electrolytic layer made of a Ba—Ce-based oxide and capable of simultaneously transferring oxygen and hydrogen.

FIG. 11 shows the structure of the limiting-current type hydrocarbon sensor of the present example. The solid-electrolytic layer 3 of the limiting-current type hydrocarbon sensor was formed of a sintered body of $BaCe_{0.8}Gd_{0.2}O_{3-\alpha}$ having a size of 10×10 mm and a thickness of 0.45 mm, on which an anode 2 and a cathode 4, both being made of platinum, were baked. Over the anode, a hydrocarbon diffusion rate determining layer was formed of a ceramic substrate 1 and a spacer 6. Furthermore, the solid-electrolytic layer 50 of the solid ion pump 5 for transferring oxygen, hydrogen and water vapor was formed of a sintered body of $BaCe_{0.8}Gd_{0.2}O_{3-\alpha}$ having a size of 10×10 mm and a thickness of 0.5 mm, and the pair of electrodes 51, 52 of the pump were made of platinum. This solid ion pump was adhered to the sensor-use solid-electrolytic layer 3 on the cathode side with a space provided therebetween.

The effect of oxygen on the output of the sensor of the present example was examined by using a gas similar to the atmosphere. A mixture gas of butane, nitrogen and 4% water was used as a gas to be measured, and the concentration of oxygen was changed in the range of 0 to 2%. The sensor was placed in an electric furnace maintained at 700° C., and the output of the sensor was examined when the concentration of butane was changed in the range of 0 to 1%. At this time, the drive voltage of the solid ion pump was set at a fixed value of 1.0 V and applied in the direction of pumping oxygen to the inside and in the opposite direction of transferring oxygen from the inside. The output of the sensor was observed in the two directions.

Figure 15:
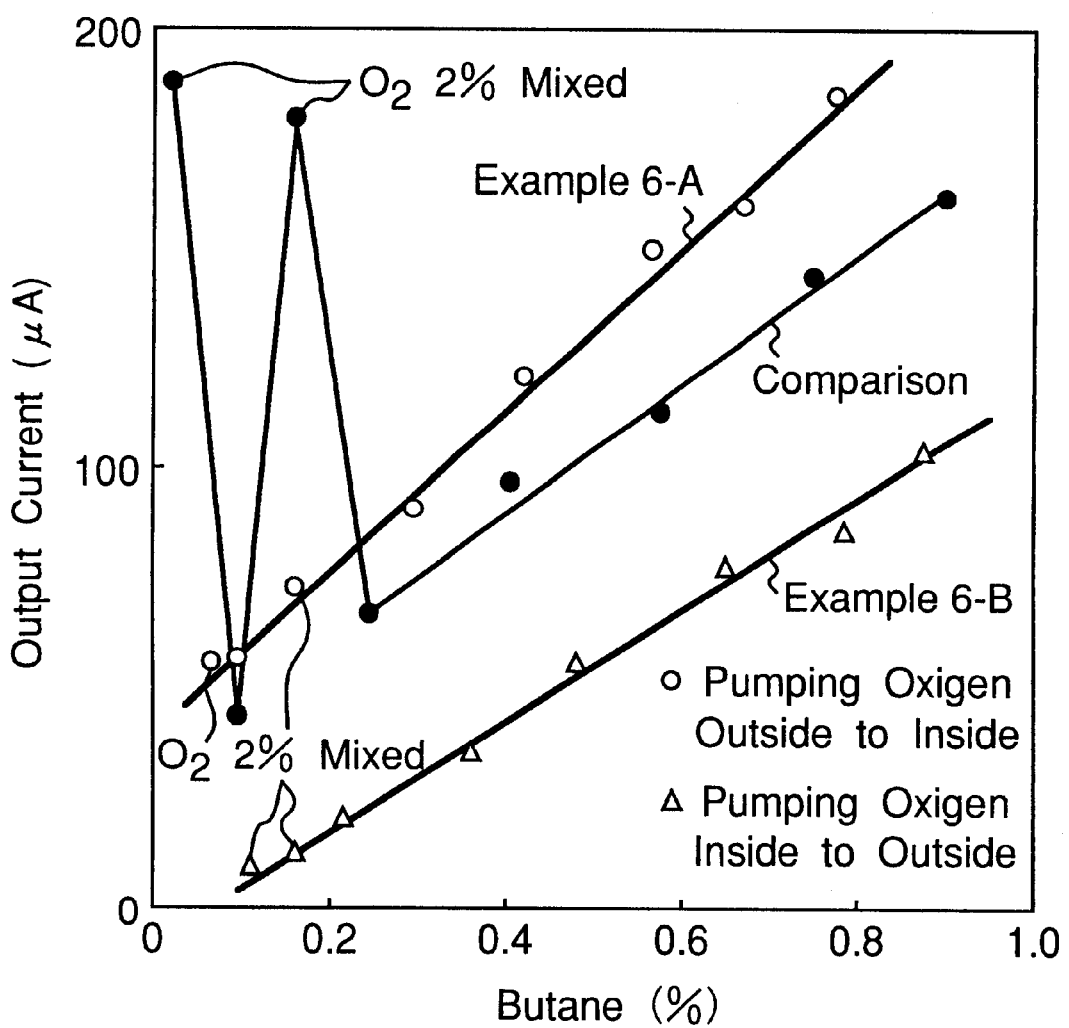
FIG. 15 is a graph showing the relationship between the concentration of butane in an atmosphere and the output current of the limiting-current type hydrocarbon sensor in accordance with another example of the present invention.

FIG. 15 is a graph showing the relationship between the concentration of butane and the output of the sensor, and also showing the output of a sensor not provided with the solid ion pump. Referring to this figure, it is found that the effect of oxygen in an atmosphere on the output of the sensor is unnoticeable at the time when the solid ion pump was driven. For this reason, it is obviously found that the sensor provided with the solid ion pump of the present invention can stably detect hydrocarbon, regardless of the presence or absence of oxygen.

EXAMPLE 7

The present example is a limiting-current type hydrocarbon sensor comprising a solid ion pump formed of a solid-electrolytic layer made of a Ba—Ce-based oxide, driven by the constant-current system and capable of simultaneously transferring oxygen, hydrogen and water vapor.

The structure of the sensor of the present example is similar to that of the example 6 shown in FIG. 11. In this example, a pump driven by a constant current will be described below. When the solid ion pump of the present invention is installed on the cathode side and the gas such as oxygen, hydrogen, etc. is moved by applying a constant current, the gas movement similar to that described in the case of the example 6 occurs basically. When the constant current is applied, the total movement amount of the gas can be maintained constant, and the amount of pumping can be controlled depending on the gas generated from the cathode of the sensor. Therefore, the concentration of the gas in the cathode chamber can be controlled easily, whereby hydrocarbon can be detected accurately.

The effect of oxygen on the output of the sensor of the present example was examined by using a gas similar to the atmosphere in the same way as that of the example 3. In the case of the present example, a constant current of 100 $\mu A$ was supplied to drive the solid ion pump in the direction of transferring oxygen from the outside to the cathode chamber and in the opposite direction of transferring oxygen from the inside to the external atmosphere. The output of the sensor was observed in the two directions.

Figure 16:
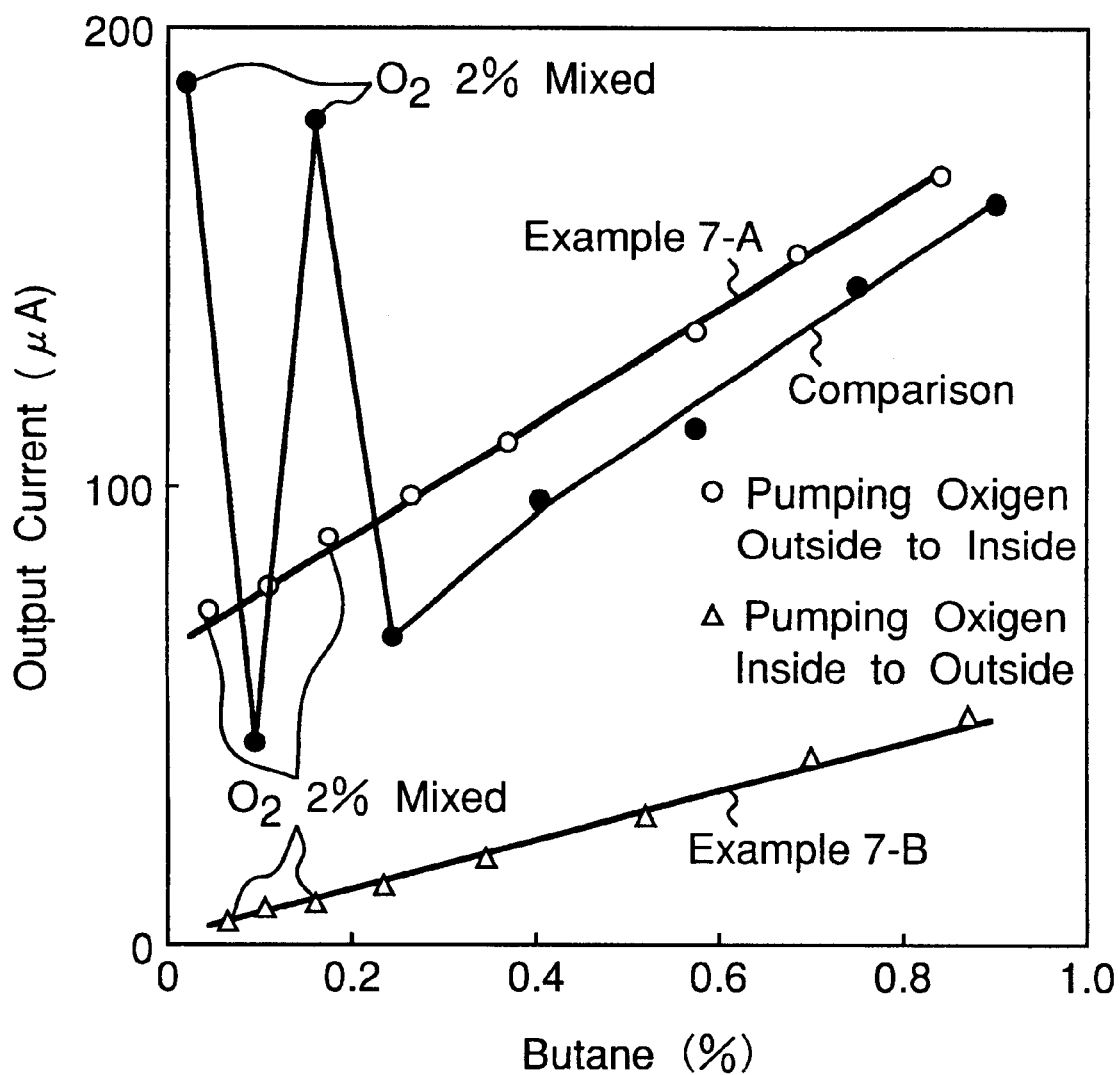
FIG. 16 is a view similar to FIG. 15, in accordance with another example of the present invention.

FIG. 16 is a graph showing the results of experiments, that is, the relationship between the concentration of butane and the output of the sensor, and also showing the output of a sensor not provided with the solid ion pump. Referring to this figure, it is found that the effect of oxygen in the atmosphere on the output of the sensor is unnoticeable at the time when the solid ion pump was driven. In addition, it is also found that the detection in the case of the constant current drive of the solid ion pump can be attained more accurately than that in the case of the constant voltage drive.

For these reasons, it is obviously found that the sensor provided with the solid ion pump of the present invention can stably detect hydrocarbon regardless of the presence or absence of oxygen.

EXAMPLE 8

The present example is an EMF-type hydrocarbon sensor provided with an oxygen pump for transferring oxygen.

FIG. 12 shows the structure of the sensor of the present example. The solid-electrolytic layer 3 for the sensor was formed of a sintered body of $BaCe_{0.8}Dy_{0.2}O_{3-\alpha}$ having a size of 10×10 mm and a thickness of 0.5 mm. On both sides of the layer, a hydrocarbon active electrode 21 and a standard electrode 41, both being made of platinum, are mounted, one electrode on each side. Next, an oxygen pump for transferring oxygen comprises a solid-electrolytic layer 50 made of zirconia including 8% of Y and a pair of platinum electrodes 51, 52. The solid ion pump was then adhered to the sensor device on the inactive electrode side thereof with an inorganic adhesive.

This EMF-type hydrocarbon sensor was placed in an electric furnace maintained at 700° C., and the atmosphere in the furnace was adjusted. Current was supplied to the oxygen pump in the direction of supplying oxygen into the sensor device (by using the inner electrode 51 as a positive electrode and the outer electrode 52 as a negative electrode). The potential at the inactive electrode 41 was used as the potential at the standard electrode for oxygen, and the relationship between the concentration of butane and output EMF was examined.

A mixture gas of butane, nitrogen and 4% water was used as a gas to be measured in the test, and the concentration of oxygen was changed in the range of 0 to 2%. The sensor was placed in an electric furnace maintained at 700° C., and the output of the sensor was examined when the concentration of butane was changed in the range of 0% to 1%.

Figure 17:
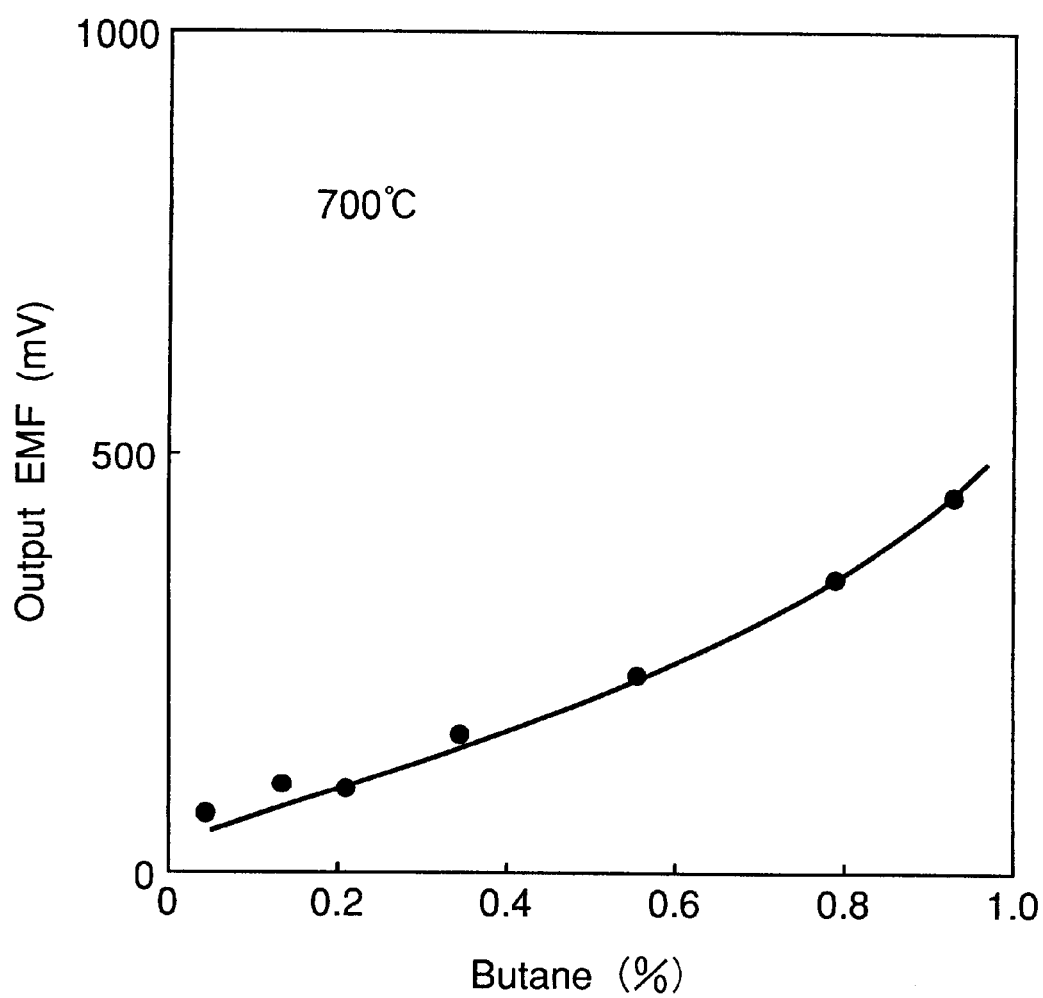
FIG. 17 is a graph showing the relationship between the concentration of gas and the EMF value of the EMF-type hydrocarbon sensor in accordance with another example of the present invention.
Figure 18:
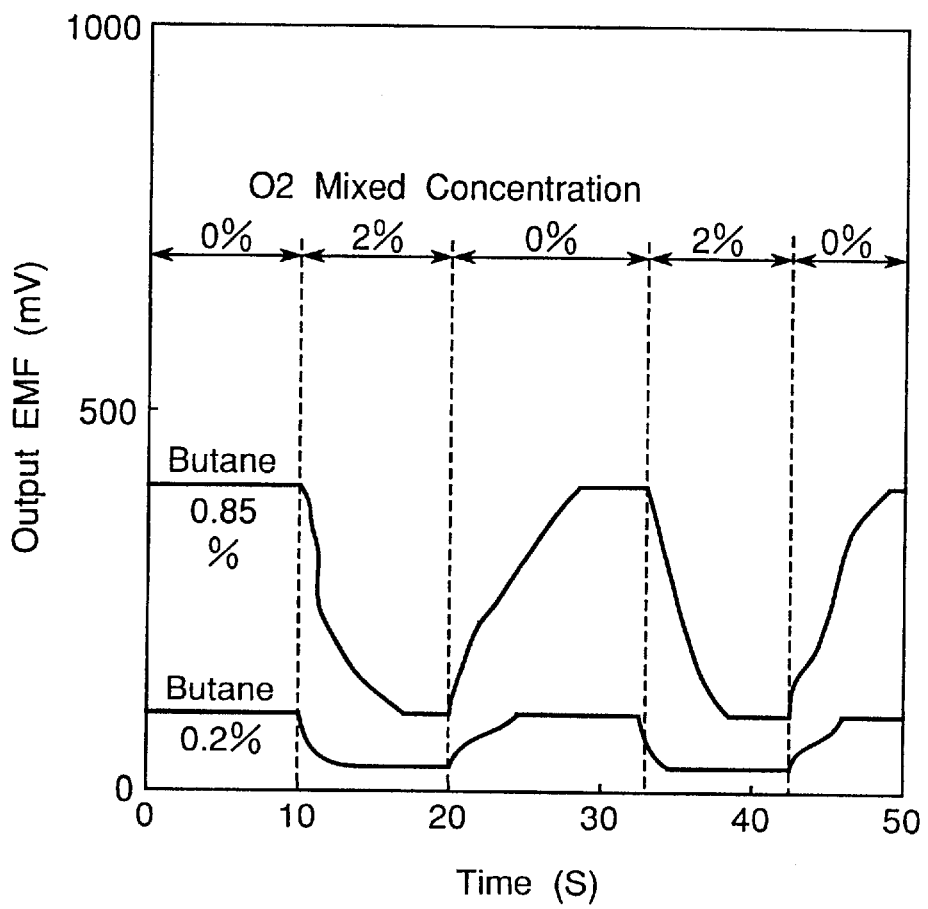
FIG. 18 is a view showing changes in the output of the EMF-type hydrocarbon sensor of the present invention at the time when the concentration of oxygen changes.
Figure 19:
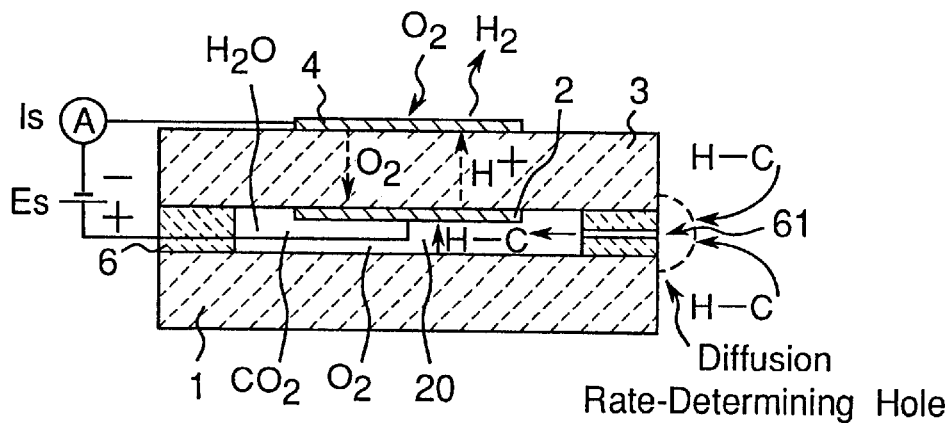
FIG. 19 is a schematic sectional view showing a conventional limiting-current type hydrocarbon sensor.

FIG. 17 shows the relationship between the concentration of the gas and EMF. Referring to the figure, it is found that there is an obvious relationship between the concentration of butane in an atmosphere and EMF. FIG. 18 shows changes in the output EMF of the sensor at the time when the concentrations of the butane under measurement have two constant levels, i.e. 0.2% and 0.85%, and when the concentration of oxygen was changed repeatedly in the range of 0% to 2%.

Referring to FIG. 18, the EMF of the sensor decreases when oxygen enters the gas under measurement. It is assumed that this decrease is caused by the combustion of the hydrocarbon component and oxygen at the hydrocarbon active electrode 21 and that the concentration of the hydrocarbon is thus decreased around the electrode. If the output of the sensor is decreased because the substantial concentration of the hydrocarbon is decreased owing to the entry of oxygen, it is assumed that the sensor has no problem as a hydrocarbon sensor in practical use.

The concentration of hydrocarbon can be measured accurately when oxygen is very lean. For this reason, the sensor provided with the solid ion pump of the present invention requires no external standard electrode, and can stably measure hydrocarbon, regardless of the presence or absence of oxygen without requiring any external standard electrode.

Platinum used as a metal for the electrodes in the Examples 4 to 8 provided with the above-mentioned ion pump, or other metals used instead of platinum, such as silver, gold and palladium, may be alloyed or mixed with other components.

Furthermore, the solid-electrolytic layer and the diffusion rate determining layer can be formed by using appropriate methods, such as the application method, the vapor deposition method, the sputtering method and the chemical-vapor deposition method (CVD method).

Moreover, the current and voltage to be applied to the sensor are not limited to those used in the above-mentioned examples, and the operation temperature of the sensor can be determined appropriately.

What is claimed is:

1. A hydrocarbon sensor comprising a thin solid-electrolytic layer capable of conducting protons and oxide ions, and an anode and cathode making contact with the surfaces of said solid-electrolytic layer,
wherein the cathode is formed of a metal layer of Al or mainly containing Al.

2. The hydrocarbon sensor according to claim 1, wherein the metal layer comprises mainly Al and at least one selected from among Si, Sn, Zn, Ga, In, Cd, Cu, Ag, Ni, Co, Fe, Mn and Cr and their oxides.

3. The hydrocarbon sensor according to claim 2, wherein the metal layer is a porous layer which is coated with an aluminum oxide film.

4. The hydrocarbon sensor according to claim 1, wherein the metal layer is a porous layer which is coated with an aluminum oxide film.

5. The hydrocarbon sensor according to claim 1, further comprising a diffusion rate determining layer connected to the solid-electrolytic layer on the side of the anode.

6. The hydrocarbon sensor according to claim 1, wherein the anode is formed of an Ag-containing layer.

7. The hydrocarbon sensor according to claim 1, wherein the solid-electrolytic layer is made of a Ba—Ce-based oxide.

8. The hydrocarbon sensor according to claim 7, wherein the solid-electrolytic layer includes a rare earth element as a third metal element in the Ba—Ce-based oxide.

9. The hydrocarbon sensor according to claim 8, wherein the rare earth element is Gd.

10. The hydrocarbon sensor according to claim 1, wherein the hydrocarbon sensor is sensitive in a temperature range of 300 to 800° C. during operation of said sensor.

11. A hydrocarbon sensor comprising a thin sensor-use solid-electrolytic layer capable of conducting protons and oxide ions, a pair of sensor-use electrodes formed on both sides of the solid-electrolytic layer, and a diffusion rate determining layer formed on the side of an anode of the pair of sensor-use electrodes,
wherein a solid ion pump for transferring oxygen, hydrogen or water is provided on the surface of the sensor-use solid-electrolytic layer on the side of a cathode which is the other of said pair of sensor-use electrodes, between the cathode and an atmosphere under measurement.

12. The hydrocarbon sensor according to claim 11, wherein the solid ion pump comprises a pump-use solid-electrolytic layer for covering the surface of the sensor-use solid-electrolytic layer on the cathode side, and a pair of pump-use electrodes which is attached on the surfaces of the pump-use solid-electrolytic layer.

13. The hydrocarbon sensor according to claim 12, wherein the solid-electrolytic layer for the solid ion pump contains an oxide or mixed oxides of at least one element selected from among Zr, Ce, Bi, Ca, Ba and Sr.

14. The hydrocarbon sensor according to claim 12, wherein the solid ion pump transfers oxygen and hydrogen simultaneously.

15. The hydrocarbon sensor according to claim 12, wherein the solid-electrolytic layer for the solid ion pump is made of an oxide including at least Ba and Ce.

16. The hydrocarbon sensor according to claim 12, which is operable at a constant voltage across the pair of electrodes on the pump-use solid-electrolytic layer to drive the solid ion pump.

17. The hydrocarbon sensor according to claim 12, which is operable at a constant current across the pair of electrodes on the pump-use solid-electrolytic layer to drive the solid ion pump.

18. The hydrocarbon sensor according to claim 11, wherein the solid ion pump transfers oxygen or hydrogen.

19. The hydrocarbon sensor according to claim 11, wherein the sensor-use solid-electrolytic layer is made of an oxide including at least Ba and Ce.

20. The hydrocarbon sensor according to claim 11, wherein the cathode for the sensor is formed of a metal layer of Al or mainly containing Al.

21. The hydrocarbon sensor according to claim 20, wherein the metal layer mainly comprises Al and includes at least one selected from the group containing Si, Sn, Zn, Ga, In, Cd, Cu, Ag, Ni, Co, Fe, Mn and Cr and their oxides.

22. The hydrocarbon sensor according to claim 20, wherein the metal layer is a porous layer which is coated with an aluminum oxide film.

23. An EMF hydrocarbon sensor comprising a sensor-use solid-electrolytic layer capable of conducting protons and oxide ions, and a pair of sensor-use electrodes formed on both sides of the solid-electrolytic layer,
wherein said sensor further comprises a solid ion pump for supplying oxygen to any one of the sensor-use electrodes from a atmosphere to be measured.

24. The hydrocarbon sensor according to claim 23, wherein the solid ion pump comprises a pump-use solid-electrolytic layer capable of conducting oxygen which covers the sensor-use solid-electrolytic to provide space over the sensor-use electrode, and a pair of electrodes attached on both sides of the pump-use solid-electrolytic layer.

25. The hydrocarbon sensor according to claim 24, wherein the pump-use solid-electrolytic layer being made of an oxide including at least one element selected from a group containing Zr, Ce, Bi, Ba and Sr.

26. The hydrocarbon sensor according to claim 23, wherein the sensor-use solid-electrolytic layer is made of an oxide including at least Ba and Ce.

* * * * *